US005772601A

United States Patent [19]

Oka et al.

[11] Patent Number: 5,772,601
[45] Date of Patent: Jun. 30, 1998

[54] APPARATUS FOR EVALUATING CARDIAC FUNCTION OF LIVING SUBJECT

[75] Inventors: Tohru Oka, Ichinomiya; Hideichi Tsuda, Komaki, both of Japan

[73] Assignee: Colin Corporation, Komaki, Japan

[21] Appl. No.: 703,360

[22] Filed: Aug. 26, 1996

[51] Int. Cl.$^6$ .................................................. A61B 5/29
[52] U.S. Cl. ................................................... 600/495
[58] Field of Search .................................. 128/670, 700, 128/680

[56] References Cited

U.S. PATENT DOCUMENTS 5,178,151  1/1993  Sackner .................................. 128/672

*Primary Examiner*—Scott M. Getzow
*Attorney, Agent, or Firm*—Oliff & Berridge, PLC

[57] ABSTRACT

An apparatus for evaluating a blood-ejecting function of a heart of a living subject, including a pressure pulse wave sensor which is adapted to be worn on a body portion of the subject to detect a pressure pulse wave which is produced from an artery of the subject in synchronism with a heartbeat of the subject, a first determining device for determining a first value of an index corresponding to a systolic area which is defined by a waveform of a first heartbeat-synchronous pulse of the pressure pulse wave detected by the pressure pulse wave sensor before the subject undergoes a physical exercise, a second determining device for determining a second value of the index corresponding to a systolic area which is defined by a waveform of a second heartbeat-synchronous pulse of the pressure pulse wave detected by the pressure pulse wave sensor after the subject undergoes the physical exercise, and an evaluating device for evaluating the blood-ejecting function of the heart of the subject, based on the determined first and second values of the index.

27 Claims, 26 Drawing Sheets

FIG.12A
MAGNITUDE
MA OF DISTAL-
SIDE K SOUND
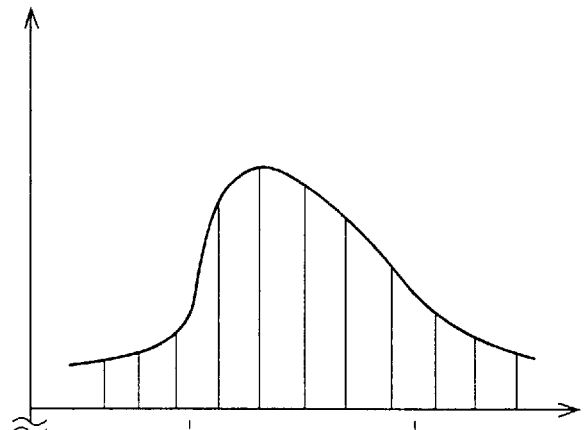
FIG.12B
DELAY TIME
DT (msec)
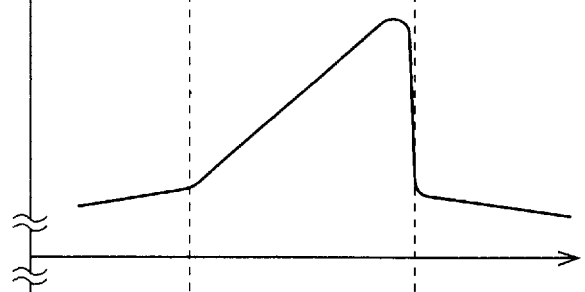
FIG.12C
EVALUATION
VALUE
L ($P_k$)
$P_{KSYS}$     $P_{KDIA}$
CUFF PRESSURE $P_k$ (mmHg)

APPARATUS FOR EVALUATING CARDIAC FUNCTION OF LIVING SUBJECT

BACKGROUND OF THE INVENTION

1. Field of the Invention

The present invention relates to an apparatus for evaluating a cardiac function of a living subject such as a human being.

2. Related Art Statement

The blood-ejecting function of the heart of a living subject becomes more active when the subject undergoes an exercise test, and recovers back to its resting condition after the test. The volume of cardiac blood ejection is defined as the product of stroke volume (i.e., amount of blood ejected per stroke), SV, and heart rate, HR. Thus, it may be judged whether the cardiac blood-ejecting function of the subject is normal or not, by observing how the heart rate HR of the subject recovers back to its resting condition or value after the exercise test.

Silent myocardial ischemia is one of heart diseases. Since this disease is "silent" to the patient, i.e., is not perceived by the patient, an accurate diagnosis should be made. However, this disease is characterized by lowered stroke volume SV, and accordingly the heart rate HR may not be relied upon in judging whether the cardiac blood-ejecting function of the patient is normal or not.

SUMMARY OF THE INVENTION

It is a first object of the present invention to provide an apparatus for providing accurate physical information relating to a cardiac blood-ejecting function of a living subject.

It is a second object of the present invention to provide an apparatus for evaluating, with accuracy, a cardiac blood-ejecting function of a living subject.

It is a third object of the present invention to provide an apparatus for providing accurate physical information relating to a myocardial ischemia of a living subject.

It is a fourth object of the present invention to provide an apparatus for non-invasively evaluating, with accuracy, a myocardial ischemia of a living subject.

It is a fifth object of the present invention to provide an apparatus for non-invasively evaluating, with accuracy, a cardiac blood-ejecting function of a living subject.

The above-indicated first object has been achieved according to a first aspect of the present invention, which provides an apparatus for providing physical information relating to a blood-ejecting function of a heart of a living subject, comprising a pressure pulse wave sensor which is adapted to be worn on a body portion of the subject to detect a pressure pulse wave produced from an artery of the subject in synchronism with a heartbeat of the subject, first determining means for determining a first value of an index corresponding to a systolic area which is defined by a waveform of a first heartbeat-synchronous pulse of the pressure pulse wave detected by the pressure pulse wave sensor before the subject undergoes a physical exercise, second determining means for determining a second value of the index corresponding to a systolic area which is defined by a waveform of a second heartbeat-synchronous pulse of the pressure pulse wave detected by the pressure pulse wave sensor after the subject undergoes the physical exercise, and a display device which displays, as the physical information, the determined first and second values of the index in comparison with each other, so that an observer evaluates the blood-ejecting function of the heart of the subject based on the determined first and second values of the index displayed by the display device.

The systolic area which is defined by the waveform of each heartbeat-synchronous pulse of a pulse wave produced from an artery of a living subject corresponds to the stroke volume SV of the heart of the subject. The Applicants of the present application has found that an index relating to the systolic area takes different values before and after the subject undergoes a physical exercise and that the blood-ejecting function of the heart of the subject can be evaluated with accuracy by utilizing the difference of the index values, irrespective of whether the subject suffers from myocardial ischemia. Thus, the myocardial ischemia can be diagnosed with accuracy according to the principle of the present invention. In the physical-information providing apparatus in accordance with the first aspect of the invention, the display device displays the first index value determined with respect to the waveform of the pressure pulse wave detected before the physical exercise of the subject, and the second index value determined after the exercise, in comparison with each other. Therefore, an observer can easily evaluate the blood-ejecting function of the heart of the subject based on the first and second index values displayed by the display device, for example, the amount or rate of change of the second value from the first value or the time or rate of recovering of the second value back to a value substantially equal to the first value. Silent myocardial ischemia can be diagnosed by accurately evaluating the cardiac blood-ejecting function of the subject.

According to a preferred feature of the first aspect of the invention, the apparatus further comprises evaluating means for evaluating the blood-ejecting function of the heart of the subject, based on the determined first and second values of the index, and the display device displays information indicative of a result of evaluation of the blood-ejecting function by the evaluating means.

According to another feature of the first aspect of the invention, the apparatus further comprises a blood pressure measuring device which measures a blood pressure of the subject, the blood pressure measuring device including an inflatable cuff which is adapted to be worn on the subject, and calibrating means for determining a first relationship between blood pressure and magnitude of the pressure pulse wave, based on at least one magnitude of at least one heartbeat-synchronous pulse of the pressure pulse wave detected by the pressure pulse wave sensor before the subject undergoes the physical exercise, and at least one blood pressure value of the subject measured by the blood pressure measuring device before the subject undergoes the physical exercise, and determining a second relationship between blood pressure and magnitude of the pressure pulse wave, based on at least one magnitude of at least one heartbeat-synchronous pulse of the pressure pulse wave detected by the pressure pulse wave sensor after the subject undergoes the physical exercise, and at least one blood pressure value of the subject measured by the blood pressure measuring device after the subject undergoes the physical exercise, the calibrating means calibrating, according to the first relationship, the waveform of the first heartbeat-synchronous pulse and calibrating, according to the second relationship, the waveform of the second heartbeat-synchronous pulse, the first determining means determining the first value of the index corresponding to the systolic area defined by the calibrated waveform of the first heartbeat-synchronous pulse, the second determining means determining the second value of the index corresponding to the systolic area defined by the calibrated waveform of the second heartbeat-synchronous pulse.

According to another feature of the first aspect of the invention, the apparatus further comprises a blood-pressure measuring device comprising an inflatable cuff which is adapted to be worn on the subject, a distal and a proximal microphone which are provided at a distal and a proximal position on the cuff worn on the subject, respectively, and which detect a plurality of distal arterial sounds at the distal position and a plurality of proximal arterial sounds at the proximal position, respectively, while a pressure in the cuff is changed, delay-time determining means for determining a delay time of a time of detection of each of the distal arterial sounds detected by the distal microphone, from a time of detection of a corresponding one of the proximal arterial sounds detected by the proximal microphone, curve providing means for determining a product of each of respective magnitudes of the distal arterial sounds and a corresponding one of the respective delay times of the distal arterial sounds, and providing a curve by connecting the respective determined products with one another along an axis indicative of the pressure of the cuff, and blood-pressure determining means for determining a blood pressure of the subject based on the curve provided by the curve providing means.

The above-indicated second object has been achieved according to a second aspect of the present invention, which provides an apparatus for evaluating a blood-ejecting function of a heart of a living subject, comprising a pressure pulse wave sensor which is adapted to be worn on a body portion of the subject to detect a pressure pulse wave which is produced from an artery of the subject in synchronism with a heartbeat of the subject, first determining means for determining a first value of an index corresponding to a systolic area which is defined by a waveform of a first heartbeat-synchronous pulse of the pressure pulse wave detected by the pressure pulse wave sensor before the subject undergoes a physical exercise, second determining means for determining a second value of the index corresponding to a systolic area which is defined by a waveform of a second heartbeat-synchronous pulse of the pressure pulse wave detected by the pressure pulse wave sensor after the subject undergoes the physical exercise, and evaluating means for evaluating the blood-ejecting function of the heart of the subject, based on the determined first and second values of the index.

In the blood-ejecting-function evaluating apparatus in accordance with the second aspect of the invention, the evaluating means evaluate the blood-ejecting function of the heart of the subject, based on the first index value determined with respect to the waveform of the pressure pulse wave detected before the exercise, and the second index value determined after the exercise. Therefore, the present apparatus can evaluate the blood-ejecting function with accuracy. In addition, silent myocardial ischemia can be diagnosed based on the accurate evaluation of the blood-ejecting function of the heart of the subject.

According to a preferred feature of the second aspect of the invention, the evaluating means comprises first means for evaluating the blood-ejecting function of the heart of the subject, based on at least one of an amount of change of the determined second value from the determined first value and a rate of change of the determined second value from the determined first value.

According to another feature of the second aspect of the invention, the first means of the evaluating means comprises judging means for judging whether the blood-ejecting function of the heart of the subject is normal, by comparing the one of the amount of change and the rate of change with a corresponding one of a first reference value and a second reference value. This judgment can be made with ease and accordingly no complex algorithm is needed to make this judgment.

According to another feature of the second aspect of the invention, the second determining means comprises means for determining a plurality of the second values of the index each of which corresponds to a systolic area defined by a waveform of a corresponding one of a plurality of the second heartbeat-synchronous pulses of the pressure pulse wave detected by the pressure pulse wave sensor after the subject undergoes the physical exercise, and the evaluating means comprises second means for evaluating the blood-ejecting function of the heart of the subject, based on at least one of a time of recovering of the determined second values back to a value substantially equal to the determined first value and a rate of recovering of the determined second values back to a value substantially equal to the determined first value. In this case, the blood-ejecting function of the heart of the subject can be evaluated with higher accuracy.

According to another feature of the second aspect of the invention, the second means of the evaluating means comprises judging means for judging whether the blood-ejecting function of the heart of the subject is normal, by comparing the one of the time of recovering and the rate of recovering with a corresponding one of a third reference value and a fourth reference value.

According to another feature of the second aspect of the invention, the apparatus further comprises converting means for converting the waveform of each of the first and second heartbeat-synchronous pulses, to a converted waveform, according to a predetermined mathematical transfer function defining a relationship between a waveform of a heartbeat-synchronous pulse of a pulse wave detected in an aorta of the subject and a waveform of a corresponding heartbeat-synchronous pulse of a pulse wave detected from the artery of the body portion of the subject, the first determining means determining the first value of the index corresponding to the systolic area defined by the converted waveform of the first heartbeat-synchronous pulse, the second determining means determining the second value of the index corresponding to the systolic area defined by the converted waveform of the second heartbeat-synchronous pulse. In this case, the first and second index values are determined with higher accuracy based on the waveform of the intra-aortic pulse wave, and accordingly the blood-ejecting function can be evaluated with higher accuracy based on the first and second index values.

According to another feature of the second aspect of the invention, the apparatus further comprises a blood pressure measuring device which measures a blood pressure of the subject, the blood pressure measuring device including an inflatable cuff which is adapted to be worn on the subject, and calibrating means for determining a first relationship between blood pressure and magnitude of the pressure pulse wave, based on at least one magnitude of at least one heartbeat-synchronous pulse of the pressure pulse wave detected by the pressure pulse wave sensor before the subject undergoes the physical exercise, and at least one blood pressure value of the subject measured by the blood pressure measuring device before the subject undergoes the physical exercise, and determining a second relationship between blood pressure and magnitude of the pressure pulse wave, based on at least one magnitude of at least one heartbeat-synchronous pulse of the pressure pulse wave detected by the pressure pulse wave sensor after the subject undergoes the physical exercise, and at least one blood pressure value of the subject measured by the blood pressure measuring device after the subject undergoes the physical exercise, the calibrating means calibrating, according to the first relationship, the waveform of the first heartbeat-synchronous pulse and calibrating, according to the second relationship, the waveform of the second heartbeat-synchronous pulse, wherein the first determining means determines the first value of the index corresponding to the systolic area defined by the calibrated waveform of the first heartbeat-synchronous pulse, and the second determining means determines the second value of the index corresponding to the systolic area defined by the calibrated waveform of the second heartbeat-synchronous pulse. In this case, the calibrated waveform of the first or second heartbeat-synchronous pulse detected before or after the physical exercise of the subject represents with high accuracy the blood pressure inside the wall of the artery. Thus, no possible error in determining the change of the second value from the first value is eliminated, and the blood-ejecting function can be evaluated with higher accuracy.

According to another feature of the second aspect of the invention, the apparatus further comprises a blood-pressure measuring device comprising an inflatable cuff which is adapted to be worn on the subject, a distal and a proximal microphone which are provided at a distal and a proximal position on the cuff worn on the subject, respectively, and which detect a plurality of distal arterial sounds at the distal position and a plurality of proximal arterial sounds at the proximal position, respectively, while a pressure in the cuff is changed, delay-time determining means for determining a delay time of a time of detection of each of the distal arterial sounds detected by the distal microphone, from a time of detection of a corresponding one of the proximal arterial sounds detected by the proximal microphone, curve providing means for determining a product of each of respective magnitudes of the distal arterial sounds and a corresponding one of the respective delay times of the distal arterial sounds, and providing a curve by connecting the respective determined products with one another along an axis indicative of the pressure of the cuff, and blood-pressure determining means for determining a blood pressure of the subject based on the curve provided by the curve providing means. In the case where the blood pressure values of the subject are measured using the cuff before and after the physical exercise, it is particularly difficult to measure with accuracy the blood pressure value after the exercise, because the subject breaths hard immediately after the exercise and the blood pressure measurement using the cuff is adversely influenced by noise resulting from the physical motion of the subject due to the hard breathing. If the blood pressure values measured before and after the exercise are not accurate, the blood-ejecting function cannot be evaluated with accuracy. However, in the present embodiment, the curve significantly largely changes at two cuff-pressure values the higher one of which corresponds to a systolic blood pressure (BP) value of the subject and the lower one of which corresponds to a diastolic BP value of the subject. On the curve, those two cuff-pressure values are exaggerated or stressed because the magnitudes of the distal arterial sounds are multiplied by the corresponding delay times, respectively. Thus, the curve is free from adverse influences from noise resulting from, e.g., physical motion of the subject. Therefore, the BP measuring device can measure the BP values of the subject with higher accuracy than conventional BP measuring devices of Korotkoff-sound type or oscillometric type can. In the case where the BP values of the subject measured with high accuracy are used to calibrate the waveform of the pressure pulse wave detected before or after the exercise, the blood-ejecting function of the subject can be evaluated with higher accuracy. In addition, the accuracy of diagnosis of silent myocardial ischemia is improved.

The above-indicated third object has been achieved according to a third aspect of the present invention, which provides an apparatus for providing physical information relating to a myocardial ischemia of a heart of a living subject, comprising a continuous blood-pressure measuring device which continuously measures a blood pressure of the subject, thereby providing continuously measured blood-pressure values of the subject, first frequency-analysis means for analyzing respective frequencies of a plurality of blood-pressure fluctuating components occurring in the continuously measured blood-pressure values, thereby providing a frequency spectrum of the blood-pressure fluctuating components, the first frequency-analysis means extracting, from the continuously measured blood-pressure values, a first one of the blood-pressure fluctuating components which has a frequency lower than a frequency of a second one of the blood-pressure fluctuating components which corresponds to a respiration of the subject, and a display device which displays, as the physical information, at least one of (a1) the first blood-pressure fluctuating component extracted from the continuously measured blood pressure values provided by the blood-pressure measuring device before the subject undergoes a physical exercise and (a2) a first value of an index derived from the first blood-pressure fluctuating component obtained before the exercise, and at least one of (b1) the first blood-pressure fluctuating component extracted from the continuously measured blood pressure values provided by the blood-pressure measuring device after the subject undergoes the physical exercise and (b2) a second value of the index derived from the first blood-pressure fluctuating component obtained after the exercise, in comparison with each other, so that an observer evaluates the myocardial ischemia of the heart of the subject based on the one of the first blood-pressure fluctuating component obtained before the exercise and the first value of the index and the one of the first blood-pressure fluctuating component obtained after the exercise and the second value of the index displayed by the display device.

The Applicants of the present application has found that the frequency analysis of fluctuations of a plurality of BP values of a living subject indicates that a frequency spectrum of the fluctuations contains a low-frequency fluctuating component whose frequency is about one third of a frequency of respiration of the subject and that the magnitude of the low-frequency fluctuating component or signal changes in relation with physical exercise of the subject and shows a characteristic change when the subject suffers from myocardial ischemia. The low-frequency fluctuating component results from a delay in the reaction of blood pressure regulation system of the subject to the physical exercise, and it is speculated that the magnitude of the low-frequency component or signal is proportional to the level of activity of sympathetic nerve system of the subject. Therefore, the low-frequency fluctuating component indicates the activity of myocardium or heart muscle of the subject. If the subject suffers from myocardial ischemia, it can be found by evaluating the degree of delay in recovering of the magnitude of the low-frequency component after the exercise, back to the magnitude before the exercise, i.e., when the subject is at rest. In the physical-information providing apparatus in accordance with the third aspect of the invention, the display device displays the first BP fluctuating component obtained before the exercise and/or the first index value, and the first BP fluctuating component obtained after the exercise and/or the second index value, in comparison with each other. Thus, an observer can easily evaluate or diagnose the myocardial ischemia of the heart of the subject based on the physical information displayed by the display device. More specifically, based on the change of respective magnitudes of the first (low-frequency) BP fluctuating component obtained before and after the exercise, or the change of the second index value from the first index value, the observer may non-invasively evaluate the degree of myocardial ischemia of the subject. Since the low-frequency BP fluctuating component directly reflects the activity of vasomotor sympathetic nerve of the subject, an observer can judge whether the subject suffers from silent myocardial ischemia, with higher accuracy, than in the case where electrocardiogram (ECG) or time-wise change of heart rate (HR) of a subject that contains various fluctuating components is used for the same purpose.

According to a preferred feature of the third aspect of the invention, the apparatus further comprises a continuous pulse-interval measuring device which continuously measures a time interval between successive two heartbeat-synchronous pulses of a pulse wave of the subject, thereby providing continuously measured pulse-interval values of the subject, second frequency-analysis means for analyzing respective frequencies of a plurality of pulse-interval fluctuating components occurring in the continuously measured pulse-interval values, thereby providing a frequency spectrum of the pulse-interval fluctuating components, the second frequency-analysis means extracting, from the continuously measured pulse-interval values, one of the pulse-interval fluctuating components which has a frequency substantially equal to the frequency of the second blood-pressure fluctuating component which corresponds to the respiration of the subject, and means for determining, as the first value of the index, a ratio of a magnitude of the first blood-pressure fluctuating component to a magnitude of the one pulse-interval fluctuating component both of which are obtained before the exercise, and determining, as the second value of the index, a ratio of a magnitude of the first blood-pressure fluctuating component to a magnitude of the one pulse-interval fluctuating component both of which are obtained after the exercise.

According to another feature of the third aspect of the invention, the first frequency-analysis means comprises means for producing a signal representing the first blood-pressure fluctuating component, and the second frequency-analysis means comprises means for producing a signal representing the one pulse-interval fluctuating component.

The above-indicated fourth object has been achieved according to a fourth aspect of the present invention, which provides an apparatus for evaluating a myocardial ischemia of a heart of a living subject, comprising a continuous blood-pressure measuring device which continuously measures a blood pressure of the subject, thereby providing continuously measured blood pressure values of the subject, first frequency-analysis means for analyzing respective frequencies of a plurality of blood-pressure fluctuating components occurring in the continuously measured blood pressure values, thereby providing a frequency spectrum of the blood-pressure fluctuating components, the first frequency-analysis means extracting, from the continuously measured blood pressure values, a first one of the blood-pressure fluctuating components which has a frequency lower than a frequency of a second one of the blood-pressure fluctuating components which corresponds to a respiration of the subject, and evaluating means for evaluating the myocardial ischemia of the subject based on at least one of (a1) the first blood-pressure fluctuating component extracted from the continuously measured blood pressure values provided by the blood-pressure measuring device before the subject undergoes a physical exercise and (a2) a first value of an index derived from the first blood-pressure fluctuating component obtained before the exercise, and at least one of (b1) the first blood-pressure fluctuating component extracted from the continuously measured blood pressure values provided by the blood-pressure measuring device after the subject undergoes the physical exercise and (b2) a second value of the index derived from the first blood-pressure fluctuating component obtained after the exercise.

In the myocardial-ischemia evaluating apparatus in accordance with the fourth aspect of the invention, the evaluating means evaluates the myocardial ischemia of the subject based on the first BP fluctuating component obtained before the exercise and/or the first index value, and the first BP fluctuating component obtained after the exercise and/or the second index value. For example, the evaluating means may evaluate or diagnose the myocardial ischemia of the heart of the subject based on the change of respective magnitudes of the first (low-frequency) BP fluctuating component obtained before and after the exercise, or the change of the second index value from the first index value. Since the low-frequency BP fluctuating component directly reflects the activity of vasomotor sympathetic nerve of the subject, the present apparatus can non-invasively judge whether the subject suffers from silent myocardial ischemia, with higher accuracy, than in the case where ECG or time-wise change of heart rate HR of a subject that contains various fluctuating components is used for the same purpose.

According to a preferred feature of the fourth aspect of the invention, the apparatus further comprises a continuous pulse-interval measuring device which continuously measures a time interval between successive two heartbeat-synchronous pulses of a pulse wave of the subject, thereby providing continuously measured pulse-interval values of the subject, and second frequency-analysis means for analyzing respective frequencies of a plurality of pulse-interval fluctuating components occurring in the continuously measured pulse-interval values, thereby providing a frequency spectrum of the pulse-interval fluctuating components, the second frequency-analysis means extracting, from the continuously measured pulse-interval values, one of the pulse-interval fluctuating components which has a frequency substantially equal to the frequency of the second blood-pressure fluctuating component which corresponds to the respiration of the subject, the evaluating means comprising means for determining, as the first value of the index, a first ratio of a magnitude of the first blood-pressure fluctuating component to a magnitude of the one pulse-interval fluctuating component both of which are obtained before the exercise, and determining, as the second value of the index, a second ratio of a magnitude of the first blood-pressure fluctuating component to a magnitude of the one pulse-interval fluctuating component both of which are obtained after the exercise. The first (low-frequency) BP fluctuating component corresponds to the activity of vasomotor sympathetic nerve of the subject, whereas the one (high-frequency) pulse-interval fluctuating component corresponds to parasympathetic nerve of the subject. In the present embodiment, since the ratio of the magnitude of the low-frequency BP fluctuating component to that of the high-frequency pulse-interval fluctuating component is used as the index and the evaluation is based on the first and second values of the index determined before and after the exercise, the accuracy of the evaluation is higher than that of the evaluation based on the low-frequency BP fluctuating component only.

According to another feature of the fourth aspect of the invention, the first frequency-analysis means comprises means for producing a signal representing the first blood-pressure fluctuating component, and the second frequency-analysis means comprises means for producing a signal representing the one pulse-interval fluctuating component.

According to another feature of the fourth aspect of the invention, the evaluating means comprises means for evaluating the myocardial ischemia by judging whether at least one of an amount of change of the second ratio from the first ratio and a rate of change of the second ratio from the first ratio is greater than a corresponding one of a first reference value and a second reference value.

According to another feature of the fourth aspect of the invention, the evaluating means comprises means for determining a plurality of the second ratios after the subject undergoes the physical exercise, and evaluating the myocardial ischemia of the subject, based on at least one of a time of recovering of the determined second ratios back to a value substantially equal to the first ratio and a rate of recovering of the determined second ratios back to a value substantially equal to the determined first ratio.

According to another feature of the fourth aspect of the invention, the continuous blood-pressure measuring device comprises a pressure pulse wave sensor which is adapted to be worn on a body portion of the subject to detect a pressure pulse wave which is produced from an artery of the subject in synchronism with a heartbeat of the subject, and means for continuously determining, as the continuously measured blood-pressure values, a systolic blood-pressure value of the subject based on an upper-peak magnitude of each of a plurality of heartbeat-synchronous pulses of the pressure pulse wave detected by the pressure pulse wave sensor. Each time a systolic BP value is newly determined with respect to each of the heartbeat-synchronous pulses, the first frequency-analysis means may extract the low-frequency BP fluctuating component from a predetermined number of last determined systolic BP values including the newly determined systolic BP value. Thus, the low-frequency BP fluctuating component enjoys high accuracy.

According to another feature of the fourth aspect of the invention, the continuous pulse-interval measuring device comprises a pressure pulse wave sensor which is adapted to be worn on a body portion of the subject to detect a pressure pulse wave which is produced from an artery of the subject in synchronism with a heartbeat of the subject, and means for continuously determining, as the continuously measured pulse-interval values, a time interval between respective upper peaks of each pair of successive two pulses of a plurality of heartbeat-synchronous pulses of the pressure pulse wave detected by the pressure pulse wave sensor.

The above-indicated fifth object has been achieved according to a fifth aspect of the present invention, which provides an apparatus for evaluating a blood-ejecting function of a heart of a living subject, comprising an electrocardiograph which provides an electrocardiogram of the subject, at least one pulse-wave sensor which is adapted to be worn on the subject to detect at least one pulse wave from the subject, pre-ejection period determining means for determining a pre-ejection period between a Q point of a heartbeat-synchronous pulse of the electrocardiogram provided by the electrocardiograph, and a minimum point of a corresponding heartbeat-synchronous pulse of an intra-aortic pulse wave of the subject, based on a waveform of the electrocardiogram and a waveform of the pulse wave detected by the pulse-wave sensor, and evaluating means for evaluating the blood-ejecting function of the heart of the subject based on the pre-ejection period determined by the pre-ejection period determining means.

One of the Applicants has found that a pre-ejection period ("PEP") from a Q point of an ECG obtained from a living subject, to a rising point (i.e., minimum point) of an intra-aortic pulse wave obtained from the subject intimately relates to a cardiac blood-ejecting function of the subject. That is, since the extraction of heart muscle of a patient who suffers from myocardial ischemia is weak, the rising point of each heartbeat-synchronous pulse of the pulse wave is delayed so that the pre-ejection period PEP is prolonged. In the cardiac-function evaluating apparatus in accordance with the fifth aspect of the invention, the evaluating means evaluates the blood-ejecting function of the heart of the subject based on the pre-ejection period determined by the pre-ejection period determining means. Thus, the cardiac function of the subject is non-invasively evaluated with high accuracy.

According to a preferred feature of the fifth aspect of the invention, the pre-ejection period determining means comprises means for determining a first value of the pre-ejection period before the subject undergoes a physical exercise, and determining a second value of the pre-ejection period after the subject undergoes the physical exercise, and the evaluating means comprises means for evaluating the blood-ejecting function based on a change of the second value of the pre-ejection period relative to the first value of the pre-ejection period. When a living subject whose cardiac function is low due to myocardial ischemia undergoes an exercise test, the change of the second value of the pre-ejection period determined after the exercise, relative to the first value of the pre-ejection period determined before the exercise, advantageously reflects the low cardiac function of the subject. Therefore, the cardiac function of the subject can be evaluated with high accuracy based on the change of the pre-ejection period. The change of the pre-ejection period may be the amount or rate of change of the second value from the first value or the time or rate of recovering of the second values back to a value substantially equal to the first value.

According to another feature of the fifth aspect of the invention, the at least one pulse-wave sensor comprises a first and a second pulse-wave sensor which are adapted to be worn on a first and a second predetermined position on the subject, respectively, to detect a first and a second pulse wave from the subject, respectively.

According to another feature of the fifth aspect of the invention, the pre-ejection period determining means comprises time-difference determining means for determining a time difference between a time of detection of a heartbeat-synchronous pulse of the first pulse wave detected by the first pulse wave sensor and a time of detection of a corresponding heartbeat-synchronous pulse of the second pulse wave detected by the second pulse wave sensor, Q-point determining means for determining a first time of production of the Q point of the heartbeat-synchronous pulse of the electrocardiogram, and pre-ejection period calculating means for calculating the pre-ejection period based on the first time of the Q point determined by the Q-point determining means and the time difference determined by the time-difference determining means.

According to another feature of the fifth aspect of the invention, the pre-ejection period determining means further comprises minimum-point estimating means for estimating a second time of production of the minimum point of the corresponding heartbeat-synchronous pulse of the intra-aortic pulse wave, based on the time difference determined by the time-difference determining means, wherein the pre-ejection period calculating means calculates the pre-ejection period based on the first time determined by the Q-point determining means and the second time estimated by the minimum-point estimating means.

BRIEF DESCRIPTION OF THE DRAWINGS

The above and optional objects, features, and advantages of the present invention will better be understood by reading the following detailed description of the preferred embodiments of the invention when considered in conjunction with the accompanying drawings, in which:

FIG. 12(A) is a graph showing respective magnitudes, MA, of distal arterial sounds (i.e., Korotkoff sounds or K sounds) detected by a distal-side microphone of the apparatus of FIG. 10;

FIG. 12(B) is a graph showing respective delay times, DT, of the distal-side K sounds from corresponding proximal-side K sounds detected by a proximal-side microphone of the apparatus of FIG. 10;

FIG. 12(C) is a graph showing a curve, L, provided by the control device of the apparatus of FIG. 10;

DETAILED DESCRIPTION OF THE PREFERRED EMBODIMENTS

Referring to FIGS. 1 to 9, there will be described a blood-ejecting-function ("BEF") evaluating apparatus 8 to which the present invention is applied.

Figure 1:
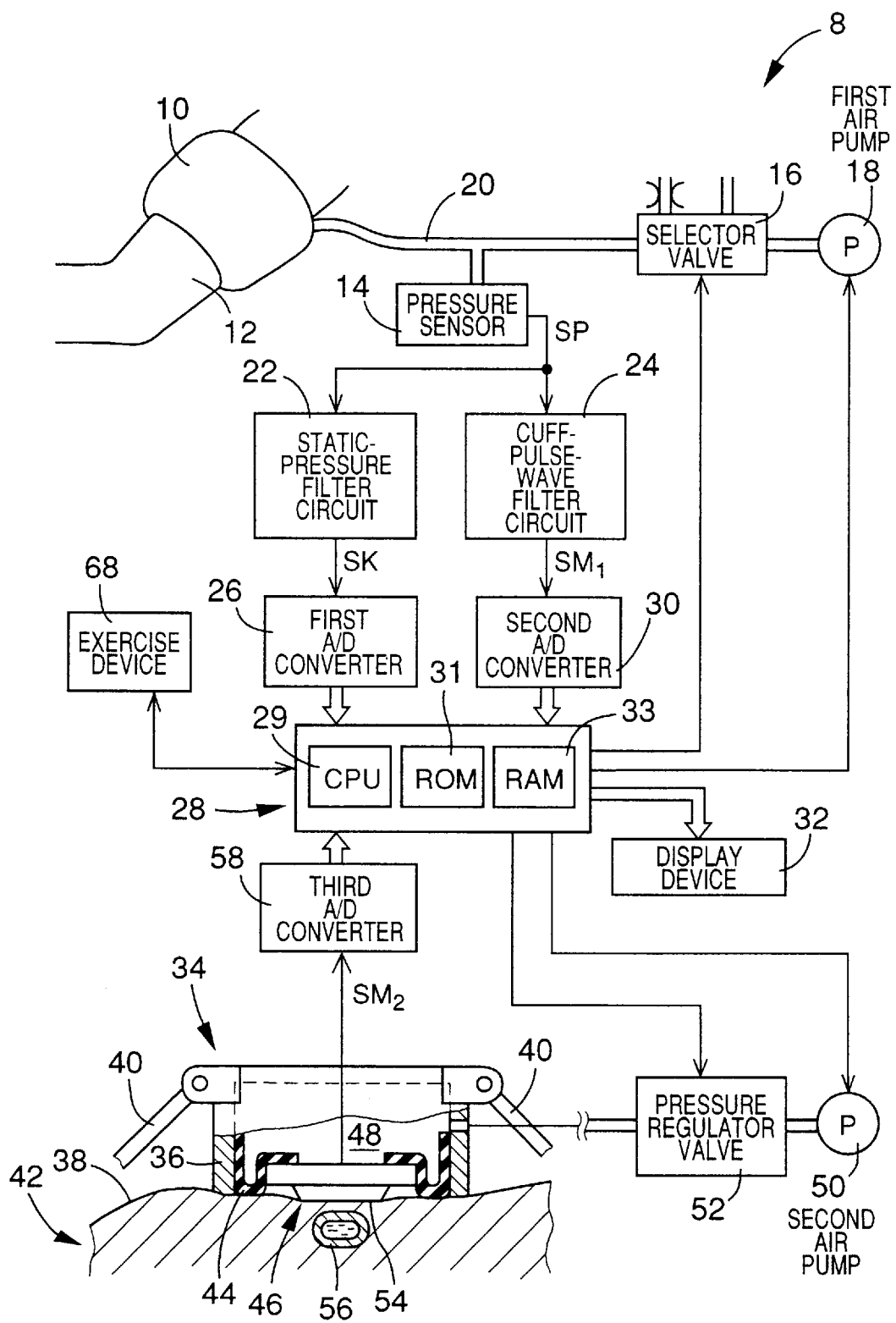
FIG. 1 is a diagrammatic view of a blood-ejecting-function ("BEF") evaluating apparatus to which the present invention is applied.

In FIG. 1, the BEF evaluating apparatus 8 includes an inflatable cuff 10 including a rubber bag and a band-like cloth bag in which the rubber bag is accommodated. The cuff 10 is wound around, e.g., an upper arm 12 of a patient as a living subject. The cuff 10 is connected via piping 20 to a pressure sensor 14, a selector valve 16, and a first air pump 18. The selector valve 16 is selectively placed, under control of an electronic control device 28, in a first state in which the valve 16 permits pressurized air to be supplied from the air pump 18 to the cuff 10 to increase quickly the air pressure of the cuff 10 (hereinafter, referred to as the "cuff pressure"), a second state in which the valve 16 causes the cuff 10 to be deflated slowly, and a third state in which the valve 16 causes the cuff 10 to be deflated quickly.

The pressure sensor 14 detects the cuff pressure (i.e., air pressure of the cuff 10), and generates a pressure signal, SP, representing the detected cuff pressure. The pressure signal SP is supplied to each of a static-pressure filter circuit 22 and a cuff-pulse-wave ("CPW") filter circuit 24. The static-pressure filter circuit 22 includes a low-pass filter which extracts, from the pressure signal SP, a cuff-pressure signal, SK, representative of a static or direct-current component, $P_k$, of the pressure signal SP. The cuff-pressure signal SK is supplied via a first analog-to-digital (A/D) converter 26 to the control device 28.

The CPW filter circuit 24 includes a band-pass filter which extracts, from the pressure signal SP, a cuff-pulse-wave ("CPW") signal, $SM_1$, representative of an oscillating or alternating-current component of the pressure signal SP. The CPW signal $SM_1$ is supplied via a second A/D converter 30 to the control device 28. The alternating-current component represented by the CPW signal $SM_1$ corresponds to an oscillatory pressure wave, i.e., pulse wave which is produced from a brachial artery (not shown) of the patient in synchronism with the heartbeat of the patient and is propagated via skin tissue to the cuff 10. This pulse wave is referred to as the "cuff pulse wave" ("CPW") to be distinguished from a "pressure pulse wave" ("PPW") which will be described later. In the present embodiment, the cuff 10, the pressure sensor 14, and the CPW filter circuit 24 cooperate with one another to provide a first pulse wave sensor.

The control device 28 is provided by a microcomputer including a central processing unit (CPU) 29, a read only memory (ROM) 31, a random access memory (RAM) 33, and an input and output (I/O) port (not shown). The CPU 29 processes input signals, including the signals SK, $SM_1$, by utilizing the temporary-storage function of the RAM 33, according to control programs pre-stored in the ROM 31. In addition, the CPU 29 supplies drive signals via the I/O port to drive circuits (not shown) associated with the selector valve 16 and the air pump 18, respectively. Thus, the CPU 29 controls respective operations of the valve 16 and the pump 18. For example, when an oscillometric BP measurement using the cuff 10 is carried out at Step SA2 (FIG. 8), the CPU 29 controls the valve 16 and the pump 18 to increase quickly the cuff pressure $P_k$ up to a predetermined target value and subsequently decrease the cuff pressure at a low rate of 2 to 3 mmHg/sec. Based on the variation of the CPW represented by the CPW signal $SM_1$ provided by the CPW filter circuit 24 during the low-rate decreasing of the cuff pressure $P_k$, the CPU 29 determines a systolic, a mean, and a diastolic BP value of the patient, according to a known oscillometric BP measuring method. In addition, the CPU 29 controls a display device 32 to display the thus determined BP values.

A pressure-pulse-wave (PPW) detecting probe 34 includes a container-like sensor housing 36, and a fastening band 40 connected to the sensor housing 36. With the help of the fastening band 40, the PPW detecting probe 34 is detachably attached to a wrist 42 of the arm 12 of the patient on which the cuff 10 is worn, such that an opening of the sensor housing 36 is opposed to a body surface 38 of the patient. A PPW sensor 46 is secured via an elastic diaphragm 44 to inner surfaces of the sensor housing 36 such that the PPW sensor 46 is movable relative to the housing 36 and is advanceable through the opening of the housing 36 toward the body surface 38 of the patient. The sensor housing 36 and the diaphragm 44 cooperate with each other to define a pressure chamber 48, which is supplied with pressurized air from a second air pump 50 via a pressure regulator valve 52. Thus, the PPW sensor 46 is pressed on the body surface 38 with a pressing force, $P_{HD}$, corresponding to the air pressure of the pressure chamber 48. In the present embodiment, the pressing forces of the PPW sensor 46 applied to the body surface 38 or the radial artery 56 are indicated in terms of pressure values (mmHg) of the pressure chamber 48. The sensor housing 36, the diaphragm 44, the pressure chamber 48, the second air pump 50, the pressure regulator valve 52, etc. cooperate with one another to provide a pressing device which presses the PPW sensor 46 against the radial artery 56 via the body surface or skin tissue 38.

The PPW sensor 46 includes a semiconductor chip formed of a monocrystalline silicon which has a press surface 54, and a number of pressure-sensing semiconductor elements (not shown) which are arranged, in the press surface 54, in an array at a regular interval of distance (about 0.2 mm), such that the array of pressure-sensing elements extends in the direction of width of the radial artery 56. When the PPW sensor 46 is pressed against the radial artery 56 via the body surface 38 of the wrist 42, the PPW sensor 46 detects an oscillatory pressure wave, i.e., pressure pulse wave (PPW) which is produced from the radial artery 56 in synchronism with the heartbeat of the patient and is propagated via the body surface 38 to the PPW sensor 46. The PPW sensor 46 generates a PPW signal, $SM_2$, representing the detected PPW, and supplies the PPW signal $SM_2$ to the control device 28 via a third A/D converter 58. An example of the pressure pulse wave (PPW) detected by the PPW sensor 46 is shown in an upper portion of the graph of FIG. 4, along a time axis. The PPW sensor 46 provides a second pulse wave sensor.

The CPU 29 of the control device 28 processes the input signals, including the PPW signal $SM_2$, by utilizing the temporary-storage function of the RAM 33, according to the control programs pre-stored in the ROM 31, and supplies drive signals to drive circuits (not shown) associated with the second air pump 50 and the pressure regulator valve 52, respectively. Thus, the CPU 29 controls respective operations of the pump 50 and the valve 52 to regulate the pressure of the pressure chamber 48 applied to the PPW sensor 46, i.e., the pressing force of the PPW sensor 46 applied to the radial artery 56 via the body surface or skin tissue 38.

When a continuous PPW detecting operation is carried out at Step SA3 (FIG. 8), the CPU 29 determines an optimum pressing force, $P_{HDP}$, of the PPW sensor 46 applied to the radial artery 56, based on the PPW detected by the PPW sensor 46 while the pressure of the pressure chamber 48 is slowly increased to flatten an upper portion of the wall of the artery 56 as shown in FIG. 1, and controls the pressure regulator valve 52 to maintain the pressure of the chamber 48 at the determined optimum pressing force $P_{HDP}$.

Figure 2:
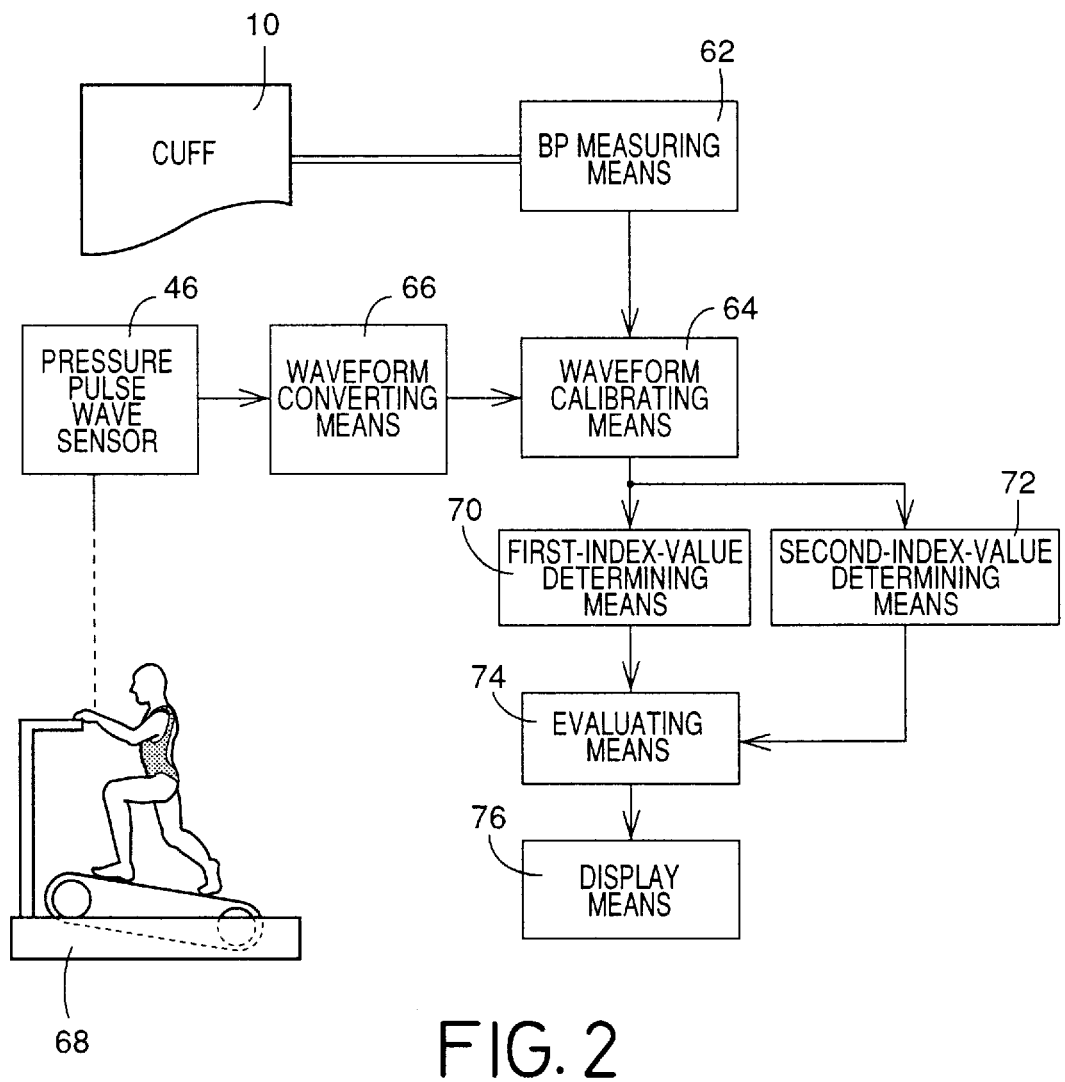
FIG. 2 is a diagrammatic view for explaining various functions of a control device of the BEF evaluating apparatus of FIG. 1.

FIG. 2 illustrates various functions of the electronic control device 28 of the present BEF evaluating apparatus 8. The pressure sensor 14 and the static-pressure and CPW filter circuits 22, 24 cooperate with the control device 28 to provide BP measuring means 62 which measures, according to an oscillometric BP measuring method (JIS T 1115; JIS is Japanese Industrial Standard), a systolic BP value $P_{BPSYS}$, a mean BP value $P_{BPMEAN}$, and a diastolic BP value $P_{BPDIA}$ of a patient based on the variation of respective amplitudes of heartbeat-synchronous pulses of the CPW detected by the first pulse wave sensor while the pressure $P_k$ Of the cuff 10 is slowly decreased or increased at the rate of 2 to 3 mmHg/sec. The CPW is represented by the CPW signal $SM_1$ provided by the CPW filter circuit 24.

Figure 3:
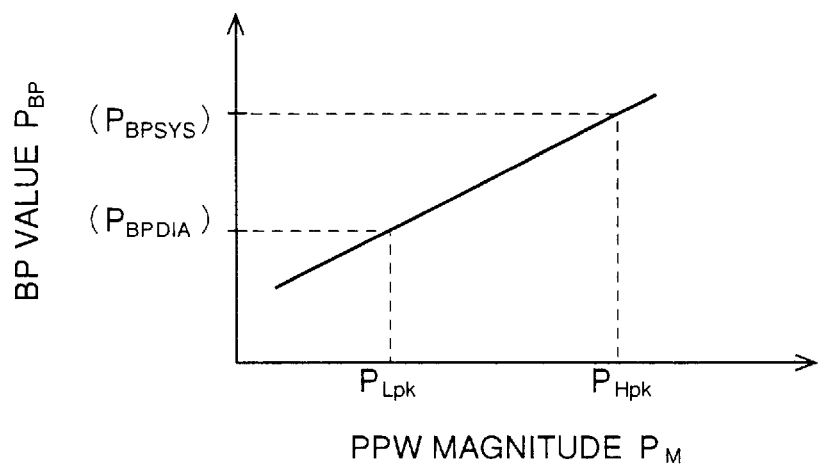
FIG. 3 is a graph showing a relationship determined by the control device of the apparatus of FIG. 1.

The PPW sensor 46 is worn on the wrist 42 of the same arm 12 of the patient as that on which the cuff 10 is worn, and detects the PPW produced from the radial artery 56 of the wrist 42. The control device 28 functions as waveform calibrating means 64 which determines a $P_{BP}$-$P_M$ relationship between BP values $P_{BP}$ and PPW magnitudes $P_M$ that is expressed by a mathematical linear function and is shown in FIG. 3, based on at least two of a first combination of an upper-peak magnitude, $P_{Hpk}$, of a heartbeat-synchronous pulse of the PPW detected by the PPW sensor 46 and a systolic BP value $P_{BPSYS}$ measured by the BP measuring means 62, a second combination of a mean magnitude of the same pulse and a measured mean BP value $P_{BPMEAN}$, and a third combination of a lower-peak magnitude, $P_{Lpk}$, of the same pulse and a measured diastolic BP value $P_{BPDIA}$. The mean magnitude of each pulse of the PPW may be defined as a height of the center of gravity of an area defined by the waveform of that pulse. The waveform calibrating means 64 determines a $P_{BP}$-$P_M$ relationship before or after the patient undergoes a physical exercise on an exercise device 68, and calibrates the waveform of the PPW detected by the PPW sensor 46 before or after the physical exercise of the patient, according to the $P_{BP}$-$P_M$ relationship determined before or after the exercise. The calibrated waveform of the PPW represents, with high accuracy, the actual change of blood pressure inside the radial artery 56.

FIG. 3 shows an example of a $P_{BP}$-$P_M$ relationship between BP values $P_{BP}$ and PPW magnitudes $P_M$ that is determined by the CPU 29. This relationship is expressed by the following linear function (1):

$$P_{BP}=A \cdot P_M+B \qquad (1)$$

where A is a constant corresponding to the slope of the linear function (1) and B is a constant corresponding to the intercept of the axis of ordinate indicative of BP values $P_{BP}$.

The selector valve 16 and the first air pump 18 cooperate with the control device 28 to provide a cuff-pressure regulating device which regulates the air pressure $P_k$ of the cuff 10 (i.e., cuff pressure $P_k$) that is detected by the pressure sensor 14 when each oscillometric BP measurement using the cuff 10 is carried out. The cuff-pressure regulating device changes the cuff pressure $P_k$ according to a well-known procedure, so that the BP measuring means 62 measures BP values of the patient using the cuff 10. For example, the regulating device increases the cuff pressure $P_k$ up to a target value, e.g., 180 mmHg, which is sufficiently higher than an estimated systolic BP value of the patient and subsequently decreases the cuff pressure $P_k$ slowly at the rate of 2 to 3 mmHg/sec, during a measurement period in which BP values of the patient are determined by the BP measuring means 62 according to a well-known oscillometric BP determining algorithm. After the BP measuring operation, the regulating device quickly deflates the cuff 10.

As shown in FIG. 2, between the PPW sensor 46 and the waveform calibrating means 64, there is provided waveform converting means 66 which converts the PPW detected by the PPW sensor 46, into a waveform which would be detected inside the aorta of the patient, according to a predetermined transfer function, TF, which describes or defines the change of PPW transmitted from the aorta to the position where the PPW sensor 46 is worn. The thus converted waveform clearly shows the rising point (i.e., minimum or lower-peak point), upper-peak point, dicrotic notch, DN, etc. of each heartbeat-synchronous pulse of the PPW. The notch DN occurs in relation with the closure of the aortic valves of patient's heart.

The exercise device 68 is provided by a well-known treadmill. However, the exercise device 68 may otherwise be provided by a different device such as an ergometer. The intensity and duration of the physical exercise may be changed within respective safe ranges, on the exercise device 68, depending upon the age, fitness, and condition of the patient.

Figure 4:
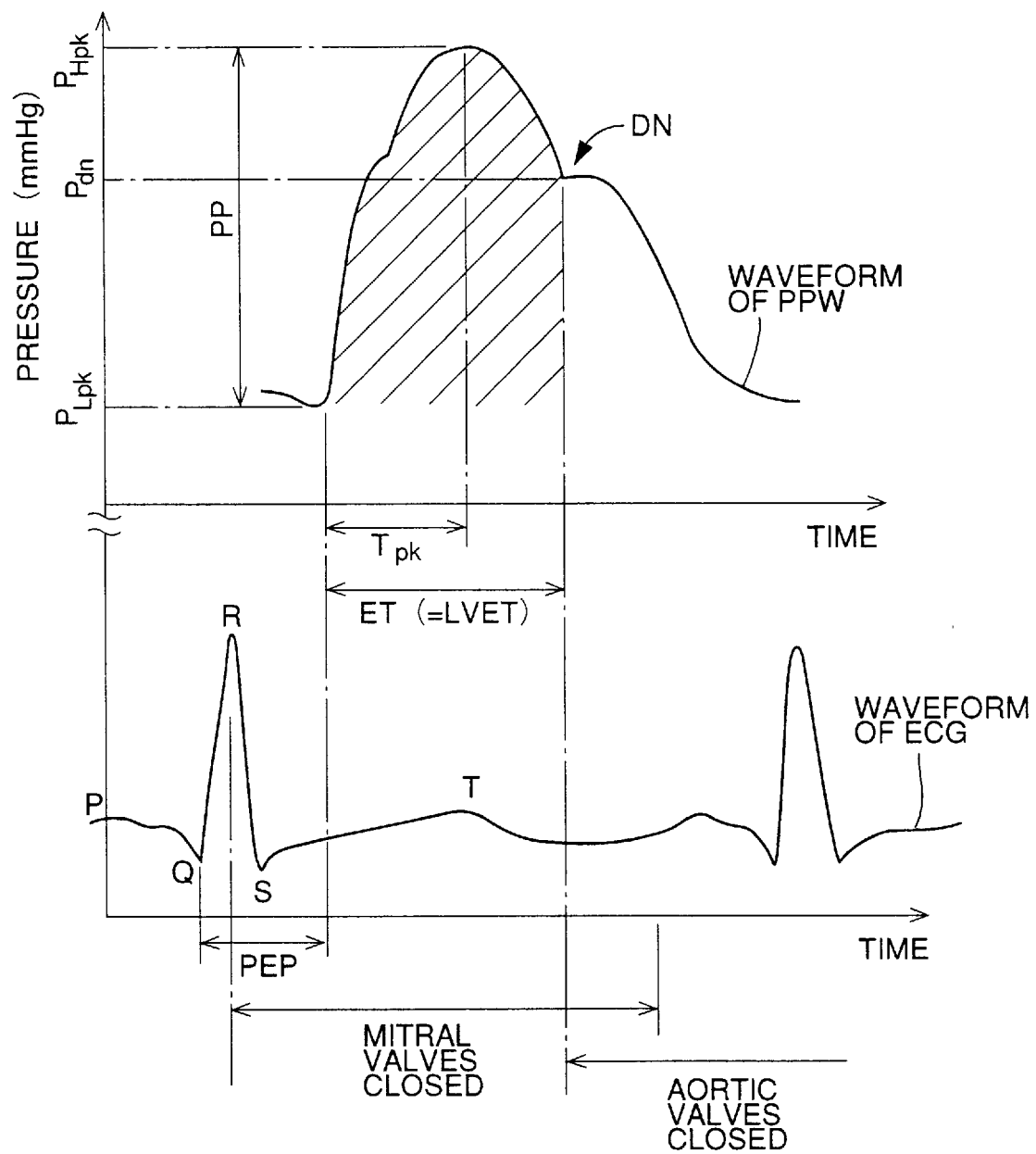
FIG. 4 is a graph showing various index parameters each of which corresponds to a systolic area, SA, defined by the waveform of a heartbeat-synchronous pulse of a pressure pulse wave ("PPW") detected by a PPW sensor of the apparatus of FIG. 1.

First-index-value determining means 70 determines a first index value, $EV_1$, corresponding to a systolic area, SA, which is defined by a systolic portion of the waveform of each heartbeat-synchronous pulse of the PPW detected by the PPW sensor 46, before the patient undergoes a physical exercise on the exercise device 68. The systolic area SA is indicated by inclined lines in the upper half of the graph of FIG. 4. FIG. 4 illustrates respective definitions of various index parameters of the waveform of each pulse of PPW. For example, a pressure value, $P_{dn}$, corresponds to the notch DN; a pulse pressure, PP, is equal to the difference between the two pressure values $P_{Hpk}$, $P_{Lpk}$ (PP=$P_{Hpk}$-$P_{Lpk}$); a pre-ejection period, PEP, is equal to the time interval between a Q wave of a heartbeat-synchronous pulse of ECG (electrocardiogram) and a rising point of a corresponding pulse of PPW; a left ventricular ejection time, ET (=LVET), is equal to the time interval between the rising point and the notch DN; and a time interval, $T_{pk}$, is equal to the interval between the rising point and the upper-peak point. The index parameter EV may be selected from a first parameter group including a ratio, $P_{dn}/P_{Hpk}$; a ratio, $P_{dn}/P_{Lpk}$; a ratio, $P_{dn}$/PP; and a ratio, PP/$P_{Lpk}$. Otherwise, the index parameter EV may be selected from a second parameter group including a ratio, PEP/ET; a ratio, $T_{pk}$/ET; and a maximum slope, $(dP/dt)_{max}$, of a rising portion of the waveform of each pulse of PPW. The rising portion of each pulse corresponds to the time interval $T_{pk}$.

It is thought that the systolic area SA of PPW indicated by inclined lines in FIG. 4 is proportional to a stroke volume, SV, of the heart of the patient. Each of the various index parameters of the first parameter group indicates how high the pressure value $P_{dn}$ corresponding to the notch DN is relative to the pressure value $P_{Lpk}$ corresponding to the lower-peak point. Meanwhile, it is thought that the shorter the ejection time ET is, the lower the pressure value $P_{Hpk}$ corresponding to the upper-peak point is. Each of the various index parameters of the second parameter group indicates how long the ejection time ET is. Anyway, each of the index parameters of the first and second parameter groups corresponds to the systolic area SA defined by the waveform of PPW, and indirectly represents the actual stroke volume of the heart of the patient.

Second-index-value determining means 72 determines a second index value, $EV_2$, corresponding to a systolic area SA defined by the waveform of PPW detected by the PPW sensor 46 after the patient undergoes the physical exercise on the exercise device 68. The second index $EV_2$ is of the same sort as that of the first index $EV_1$, that is, the single sort of index EV is selected from the above-indicated first or second parameter group. An actual value of the selected index parameter EV is determined before and after the physical exercise of the patient.

Evaluating means 74 evaluates the blood-ejecting function of the patient based on a change of the second index value $EV_2$ from the first index value $EV_1$. For example, the evaluating means 74 may evaluate the blood-ejecting function by judging whether an amount of change, $\Delta$ EV (=$EV_2$-$EV_1$), or a rate of change, $EV_2/EV_1$, of the first and second index values $EV_1$, $EV_2$ is greater than a first or second reference value, respectively. Otherwise, the evaluating means 74 may evaluate the blood-ejecting function based on a time of recovery, TR, of the second index values $EV_2$ back to a value substantially equal to the first index value $EV_1$ after the physical exercise, or a rate of recovery, * $EV_2$, of the second index values $EV_2$ after the exercise.

Figure 5:
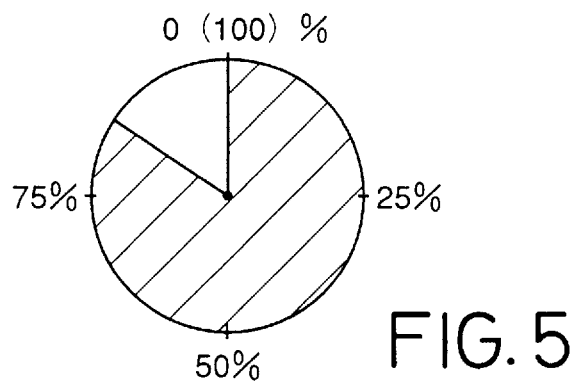
FIG. 5 is a graph showing an example of physical information which is displayed by a display device of the apparatus of FIG. 1, based on a first and a second index value determined by the apparatus of FIG. 1.
Figure 6:
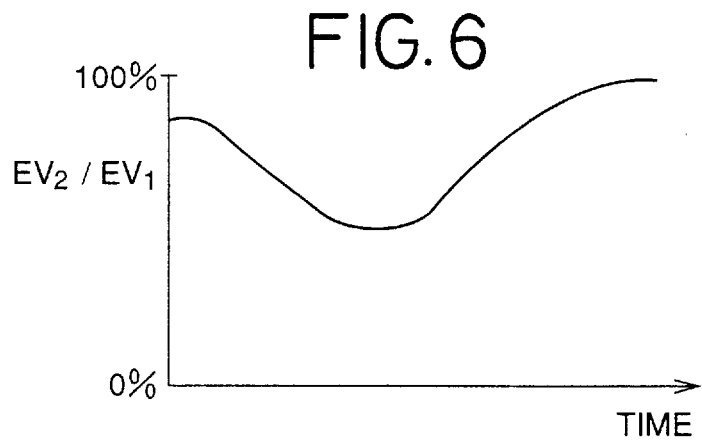
FIG. 6 is a graph showing a time-wise change of the physical information of FIG. 5 that is also displayed by the display device of the apparatus of FIG. 1.
Figure 7:
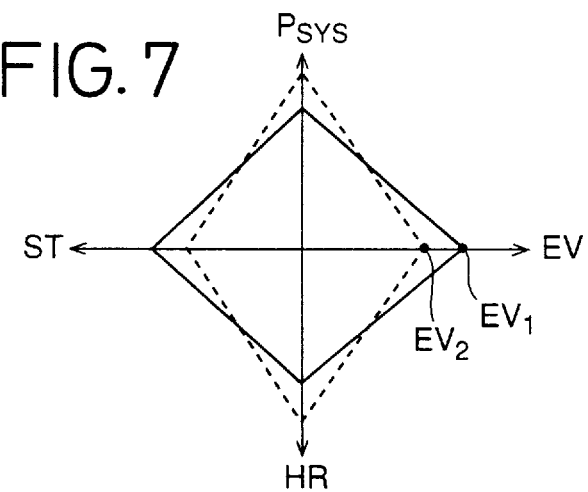
FIG. 7 is a graph showing another example of physical information which is displayed by the display device of the apparatus of FIG. 1, based on the first and second index values determined by the apparatus of FIG. 1.

Display means 76 controls the display device 32 to display the second index value $EV_2$ in comparison with the first index value $EV_1$, so that an observer can evaluate the blood-ejecting function of the patient. FIGS. 5, 6, and 7 shows examples of physical information displayed by the display device 32. FIG. 5 is a circular graph showing the percentage (%) of the second index value $EV_2$ (indicated by inclined lines) relative to the first index value $EV_1$ (100%). In FIG. 5, the second value $EV_2$ is compared with the first value $EV_1$ as 100%. FIG. 6 shows a time-wise change of ratio, $EV_2/EV_1$, (%) of the second index values $EV_2$ to the first index value $EV_1$ during and after the physical exercise. In FIG. 6, the ratio $EV_2/EV_1$ (%) is compared with 100% where $EV_2$=$EV_1$. FIG. 7 is a graph having four axes including a first axis indicative of systolic blood pressure, $P_{SYS}$; a second axis indicative of an amplitude, ST, between S wave and T wave of each pulse of ECG; a third axis indicative of heart rate, HR; and a fourth axis indicative of index parameter EV. Respective plotted values on the four axes are connected with straight lines. In FIG. 7, solid lines connect the values obtained before the exercise, and broken lines connect the values obtained after the exercise. The second index value $EV_2$ is compared with the first index value $EV_1$ on the fourth axis. Each of FIGS. 5 to 7 shows the case where the blood-ejecting function of the patient becomes low after the physical exercise.

Hereinafter, there will be described the operation of the electronic control device 28 of the BEF evaluating apparatus 8 constructed as described above, by reference to the flow chart of FIG. 8.

First, at Step SA1, the CPU 29 of the control device 28 judges whether a START switch (not shown) has been operated to start the BEF evaluating apparatus 8. While negative judgments are made at Step SA1, Step SA1 is repeated. Meanwhile, if a positive judgment is made at Step SA1, the control of the CPU 29 goes to Step SA2 to operate the BP measuring means 62 to carry out an oscillometric BP measurement using the cuff 10. This operation corresponds to a time period from point "A" to point "B" shown in FIG. 9.

At Step SA2, first, the cuff 10 is inflated up to a target pressure (e.g., 180 mmHg) sufficiently higher than an estimated systolic BP value of the patient. Then, the first air pump 18 is stopped and the selector valve 16 is switched to the second state to decrease the cuff pressure slowly at the rate of about 2 to 3 mmHg/sec. Based on the variation of respective amplitudes of heartbeat-synchronous pulses of the CPW signal $SM_1$ obtained during this slow cuff-pressure decreasing, the CPU 29 determines, according to a well-known oscillometric BP determining algorithm, a systolic, a mean, and a diastolic BP value $P_{BPSYS}$, $P_{BPMEAN}$, $P_{BPDIA}$ of the patient. In addition, based on the time interval of successive two pulses of the CPW, the CPU 29 determines a heart rate HR of the patient. The thus measured BP values and heart rate are displayed on the display device 32. Subsequently, the selector valve 16 is switched to the third state to deflate the cuff 10 quickly. This corresponds to point "B" shown in FIG. 9.

Step SA2 is followed by Step SA3 to determine a relationship between blood pressure and magnitude of PPW, based on the BP values $P_{BPSYS}$, $P_{BPDIA}$ measured at Step SA2 and magnitudes (i.e., voltages) of the PPW signal $SM_2$ produced by the PPW sensor 46. More specifically, after Step SA2, the CPU 29 reads in a length of PPW signal $SM_2$ corresponding to one heartbeat-synchronous pulse of PPW, and determines an upper-peak and a lower-peak magnitude $P_{Hpk}$, $P_{Lpk}$ of that pulse. Based on the first combination of upper-peak magnitude $P_{Hpk}$ and systolic BP value $P_{BPSYS}$ and the second combination of lower-peak magnitude $P_{Lpk}$ and diastolic BP value $P_{BPDIA}$, the CPU 29 determines a linear function defining the relationship between blood pressure $P_{BP}$ and PPW magnitude $P_M$ as shown in FIG. 3. The PPW signal $SM_2$ produced by the PPW sensor 46 is calibrated according to this relationship by the CPU 29. The thus calibrated waveform of the PPW signal $SM_2$ represents, with high accuracy, the blood pressure inside the radial artery 56 of the patient. Step SA3 corresponds to the waveform calibrating means 64 shown in FIG. 2.

Step SA3 is followed by Step SA4 to read in a predetermined number of heartbeat-synchronous pulses of PPW detected by the PPW sensor 46 before the patient undergoes the physical exercise. Step SA4 is followed by Step SA5 to convert the waveform of each pulse into the waveform which would be obtained inside the aorta of the patient. For example, a transfer function TF which defines or describes the transfer of PPW from the aorta to the position where the PPW sensor 46 is worn, is pre-determined and employed in the control program. The PPW signal $SM_2$ is divided by the transfer function TF, so that the waveform of PPW signal $SM_2$ is converted into the waveform of PPW which would be obtained in the aorta. The transfer function TF may experimentally be determined in advance by using a catheter inserted in the aorta of a human being and the PPW sensor 46 worn on a body portion of the person. Step SA5 corresponds to the waveform converting means 66.

Subsequently, at Step SA6, the CPU 29 determines an index value EV corresponding to a systolic area SA defined by the waveform of PPW detected by the PPW sensor 46 before the physical exercise is burdened on the patient on the exercise device 68. The thus determined index value EV is the first index value $EV_1$, and Step SA6 corresponds to the first-index-value determining means 70. Step SA6 is followed by Step SA7 to judge whether the physical exercise has ended, based on an output signal produced from the exercise device 68. If a negative judgment is made at Step SA7, the CPU 29 outputs a permission signal to the exercise device 68 so that the device 68 can start its operation to burden physical exercise on the patient. In response to a starting operation of the device 68 by a medical staff such as a doctor or a nurse, the device 68 starts to give physical exercise at a predetermined intensity for a predetermined time period. This corresponds to point "C" shown in FIG. 9.

While Steps SA7 and SA8 are repeated, a positive judgment is made at Step SA7, if the predetermined physical exercise ended on the exercise device 68. In this case, Step SA7 is followed by Step SA9 to judge whether a second index value $EV_2$ has been determined. While negative judgments are made at Step SA9, the control of the CPU 29 goes back to Step SA2 to carry out another BP measurement using the cuff 10. This corresponds to the time period from point "D" to point "E" shown in FIG. 9. Subsequently, Steps SA3 to SA5 are carried out to read in the PPW detected by the PPW sensor 46 after the physical exercise and convert the waveform of the thus read PPW into the waveform which would be obtained inside the aorta. Moreover, at Step SA6, the CPU 29 determines an index value EV corresponding to a systolic area SA defined by the waveform of PPW detected by the PPW sensor 46 after the physical exercise, in the same manner as that employed to determine the first index value $EV_1$. The thus determined index value EV is the second index value $EV_2$, and Step SA6 corresponds to the second-index-value determining means 72.

Once the physical exercise ends and the second index value $EV_2$ is determined, a positive judgment is made at each of Steps SA7 and SA9. This corresponds to point "F" shown in FIG. 9. Then, the control of the CPU 29 goes to Step SA10 to evaluate the blood-ejecting function of the heart of the patient based on a change of the second index value $EV_2$ relative to the first index value $EV_1$. For example, the CPU 29 may determine an index value EV with respect to each of a predetermined number of heartbeat-synchronous pulses of PPW detected by the PPW sensor 46 before the physical exercise, and may determine an average of those index values EV as the first index value $EV_1$. Similarly, the CPU 29 may determine an index value EV with respect to each of a predetermined number of pulses of PPW detected after the physical exercise, and may determine an average of those index values EV as the second index value $EV_2$. In this case, the CPU 29 judges that the blood-ejecting function of the patient is normal, if an amount of change $\Delta EV$ ($=EV_2-EV_1$) or a rate of change $EV_2/EV_1$ is greater than a predetermined first or second reference value, respectively, and judges that the blood-ejecting function is low, if the amount of change $\Delta EV$ or the rate of change $EV_1/EV_2$ is not greater than the first or second reference value, respectively. Otherwise, the CPU 29 may be adapted to judge that the blood-ejecting function is normal, if the recovery time TR of the second index values $EV_2$ determined after the exercise, back to a value equal to the first index time $EV_1$ determined before the exercise is shorter than a predetermined reference value, or if the rate of recovery (i.e., slope) $\Delta EV_2$ of the second index values $EV_2$ determined after the exercise is greater than a predetermined reference value, and judge vice versa. If the blood-ejecting function of the patient is normal, the systolic area SA defined by the waveform of PPW increases in response to the starting of the physical exercise and quickly decreases or recovers back to the initial condition before the exercise, in response to the ending of the exercise. Step SA10 corresponds to the evaluating means 74 shown in FIG. 2.

Step SA10 is followed by Step SA11 to control the display device 32 to display, on a screen thereof, the result of evaluation of the blood-ejecting function of the patient carried out at Step SA10, and the various graphical representations shown in FIGS. 5 to 7. From those representations, the medical staff can easily grasp the change of the second index value or values $EV_2$ obtained after the exercise, from the first index value or values $EV_1$ obtained before the same. Step SA11 corresponds to the display means 76 shown in FIG. 2.

As is apparent from the foregoing description, the first-index-value determining means 70 determines the first index value $EV_1$ corresponding to the systolic area SA defined by the waveform of each heartbeat-synchronous pulse of PPW detected by the PPW sensor 46 before the physical exercise of the patient, and the second-index-value determining means 72 determines the second index value $EV_2$ corresponding to the systolic area SA defined by the waveform of each pulse of PPW detected by the PPW sensor 46 after the exercise. The display device 32 displays the second index value $EV_2$ in comparison with the first index value $EV_1$. Thus, the medical staff can easily evaluate the blood-ejecting function of the patient based on the change of the second value $EV_2$ from the first value $EV_1$. Since the blood-ejecting function of the patient is evaluated with accuracy, silent myocardial ischemia can be diagnosed with accuracy on the patient by the doctor.

In addition, the evaluating means 74 easily evaluates the blood-ejecting function of patient's heart, based on the change of the second value $EV_2$ from the first value $EV_1$, e.g., the amount of change, the rate of change, and the time-wise change of the second index values $EV_2$ obtained after the exercise. Even if the medical staff is not skilled in evaluating the blood-ejecting function, the present apparatus 8 can evaluate it with accuracy. Because of the accurate evaluation of the blood-ejecting function, the doctor can make an accurate diagnosis of silent myocardial ischemia on the patient.

In the case where the evaluating means 74 evaluates the blood-ejecting function of the patient by judging whether the amount or rate of change of the second index value $EV_2$ from the first index value $EV_1$ is greater than a predetermined first or second reference value, it does not need a complex algorithm to evaluate the cardiac function.

Meanwhile, in the case where the evaluating means 74 evaluates the blood-ejecting function of the patient based on the time of recovery TR of the second index values $EV_2$ back to a value equal to the first index value $EV_1$, or the rate of change of the second index values $EV_2$, the blood-ejecting function can be evaluated with high accuracy.

Since the waveform converting means 66 converts the waveform of PPW detected by the PPW sensor 46 into the waveform of PPW which would be detected inside the aorta of the patient, according to the transfer function TF, the first and second index values $EV_1$, $EV_2$ are determined with high accuracy on the converted waveform of PPW. Thus, the accuracy of evaluation of the blood-ejecting function is improved.

The waveform calibrating means 64 determines a relationship between blood pressure and PPW magnitude based on the BP values measured by the BP measuring means 62 including the cuff 10 and the magnitudes of PPW detected by the PPW sensor 46, before or after the patient undergoes the physical exercise, and calibrates the waveform of PPW detected by the PPW sensor before or after the exercise. Thus, the waveform of PPW detected before or after the exercise is calibrated so that the calibrated waveform represents with accuracy the blood pressure inside the artery of the patient. Therefore, any error in calculating the change of the second index value $EV_2$ from the first index value $EV_1$ is eliminated, and the blood-ejecting function of the patient is evaluated with high accuracy.

In the first embodiment shown in FIGS. 1–9, the waveform converting means 66 or Step SA5 is employed for converting the waveform of PPW detected from the radial artery 56, into the waveform which would be detected from the aorta. However, the converting means 66 or Step SA5 may be omitted.

While in the first embodiment both the evaluating means 74 and the display means 76 are employed, it is possible to omit one of the two means 74, 76.

Although in the first embodiment the PPW sensor 46 is worn on a wrist of the patient to detect a PPW from the radial artery 56, it is possible to wear the PPW sensor 46 on an ankle or the neck of the patient to detect a PPW from a dorsal pedal artery or a carotid artery of the patient.

While in the first embodiment a single index parameter EV is selected from the first parameter group or the second parameter group, it is possible to employ a plurality of sorts of index parameters and evaluate the blood-ejecting function of the patient based on the determined first and second index values of each of the index parameters.

In the case where the evaluating apparatus 8 employs the ratio PEP/ET as the index parameter EV, or uses the R-wave magnitude or ST level of ECG as auxiliary information that helps medical staff to find myocardial ischemia, the apparatus 8 is provided with an electrocardiograph which produces an electrocardiogram (ECG) representing the changes of electric potential of patient's heart.

While in the first embodiment the waveform calibrating means 64 determines a $P_{BP}$-$P_M$ relationship based on the systolic and diastolic BP values of the patient measured using the cuff 10 and the upper-peak and lower-peak magnitudes of one heartbeat-synchronous pulse of PPW detected by the PPW sensor 46, it is possible to determine a $P_{BP}$-$P_M$ relationship based on the measured mean BP value and the detected mean magnitude of one pulse of PPW and at least one of the first combination of the measured systolic BP value and the detected upper-peak magnitude of one pulse of PPW and the second combination of the measured diastolic BP value and the detected lower-peak magnitude.

Although in the first embodiment the oscillometric BP measuring method is employed to measure BP values of a patient at Step SA2, it is possible to employ a Korotkoff-sound-type BP-measuring method in which a microphone is provided in association with the cuff 10 and, while the cuff pressure $P_k$ is changed, the control device 28 determines a systolic and a diastolic BP value of the patient by detecting, through the microphone, Korotkoff sounds produced from the brachial artery under the cuff 10.

Referring next to FIGS. 10 to 13, there will be described a second embodiment of the present invention. The second embodiment relates to a blood-ejecting-function ("BEF") evaluating apparatus 108 which has basically the same hardware construction as that of the BEF evaluating apparatus 8 as the first embodiment shown in FIG. 1. The following description only relates to the differences of the second embodiment from the first embodiment. The same reference numerals as used in the first embodiment are used to designate the corresponding elements or parts of the second embodiment, and the description of those elements or parts is omitted.

An inflatable cuff 10 is provided with a proximal-side microphone 110a fixed to a proximal-side portion of the cuff 10, and a distal-side microphone 10b fixed to a distal-side portion of the cuff 10. The proximal-side microphone 110a detects proximal-side K (Korotkoff) sounds produced from a proximal-side portion of a brachial artery under the proximal-side portion of the cuff 10, and produces a first K-sound signal, SSa, representing the detected proximal-side K sounds, and the distal-side microphone 110b detects distal-side K sounds produced from a distal-side portion of the brachial artery under the distal-side portion of the cuff 10, and produces a second K-sound signal, SSb, representing the detected distal-side K sounds. The two electric signals SSa, SSb are supplied to an electronic control device 128 via a K-sound filter circuit 122 and an A/D converter 126. The K-sound filter circuit 122 includes a band-pass filter which permits only a signal component having frequencies corresponding to K sounds to pass therethrough.

Figure 11:
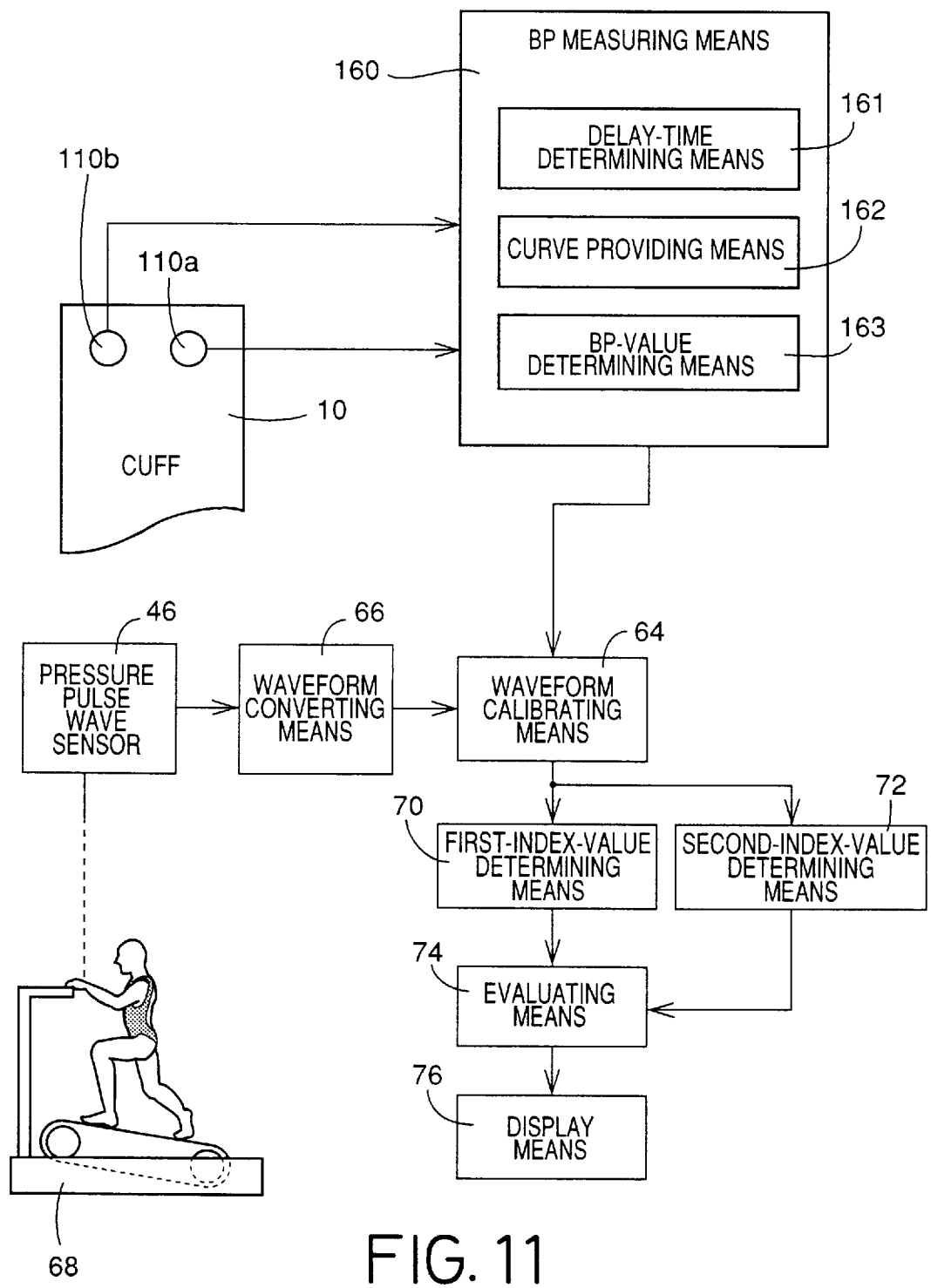
FIG. 11 is a diagrammatic view corresponding to FIG. 2, for explaining various functions of a control device of the BEF evaluating apparatus of FIG. 10.

FIG. 11 illustrates various functions of the control device 128 of the second BEF evaluating apparatus 108. The control device 128 of the second apparatus 108 is different from the control device 28 of the first apparatus 8 in that the control device 128 functions as BP measuring means 160. The BP measuring means 160 increases an air pressure $P_k$ Of the cuff 10 up to a target pressure value which is higher than an estimated systolic BP value of a living subject or a patient and subsequently decreases the cuff pressure $P_k$ slowly at the rate of 2 to 3 mmHg/sec. During this slow cuff-pressure decreasing, the proximal-side and distal-side microphones 110a, 110b detect the proximal-side and distal-side K sounds, respectively. The control device 128 determines a delay time, DT, of the time of detection of each of the distal-side K sounds from that of a corresponding proximal-side K sound, and a magnitude (i.e., amplitude), MA, of each distal-side K sound and, based on the delay times DT and the K-sound magnitudes MA, the control device 128 determines a curve, L, shown in FIG. 12(C). Moreover, based on the curve L, the control device 128 determines a systolic and a diastolic BP value $P_{BPSYS}$, $P_{BPDIA}$ of the patient.

As shown in FIG. 11, the BP measuring means 160 includes delay-time determining means 161, curve providing means 162, and BP-value determining means 163. The delay-time determining means 161 determines a delay time DT of the time of detection of each of the distal-side K sounds from that of a corresponding one of the proximal-side K sounds. The curve providing means 162 calculates the product of a magnitude MA of each of the distal-side K sounds and a corresponding one of the delay times DT, and provides a curve L connecting the thus calculated products along an axis indicative of cuff pressure $P_k$. The BP-value determining means 163 specifies two cuff-pressure values, $P_{KSYS}$, $P_{KDIA}$, where the curve L significantly largely increases and decreases as the cuff pressure $P_k$ decreases, and determines the thus specified pressure values $P_{KSYS}$, $P_{KDIA}$ as a systolic and a diastolic BP value $P_{BPSYS}$, $P_{BPDIA}$ of the patient. FIGS. 12(A) and 12(B) show the respective magnitudes MA of the distal-side K sounds detected by the distal-side microphone 110b, and the respective delay times DT of the distal-side K sounds from the corresponding proximal-side K sounds, respectively.

Figure 8:
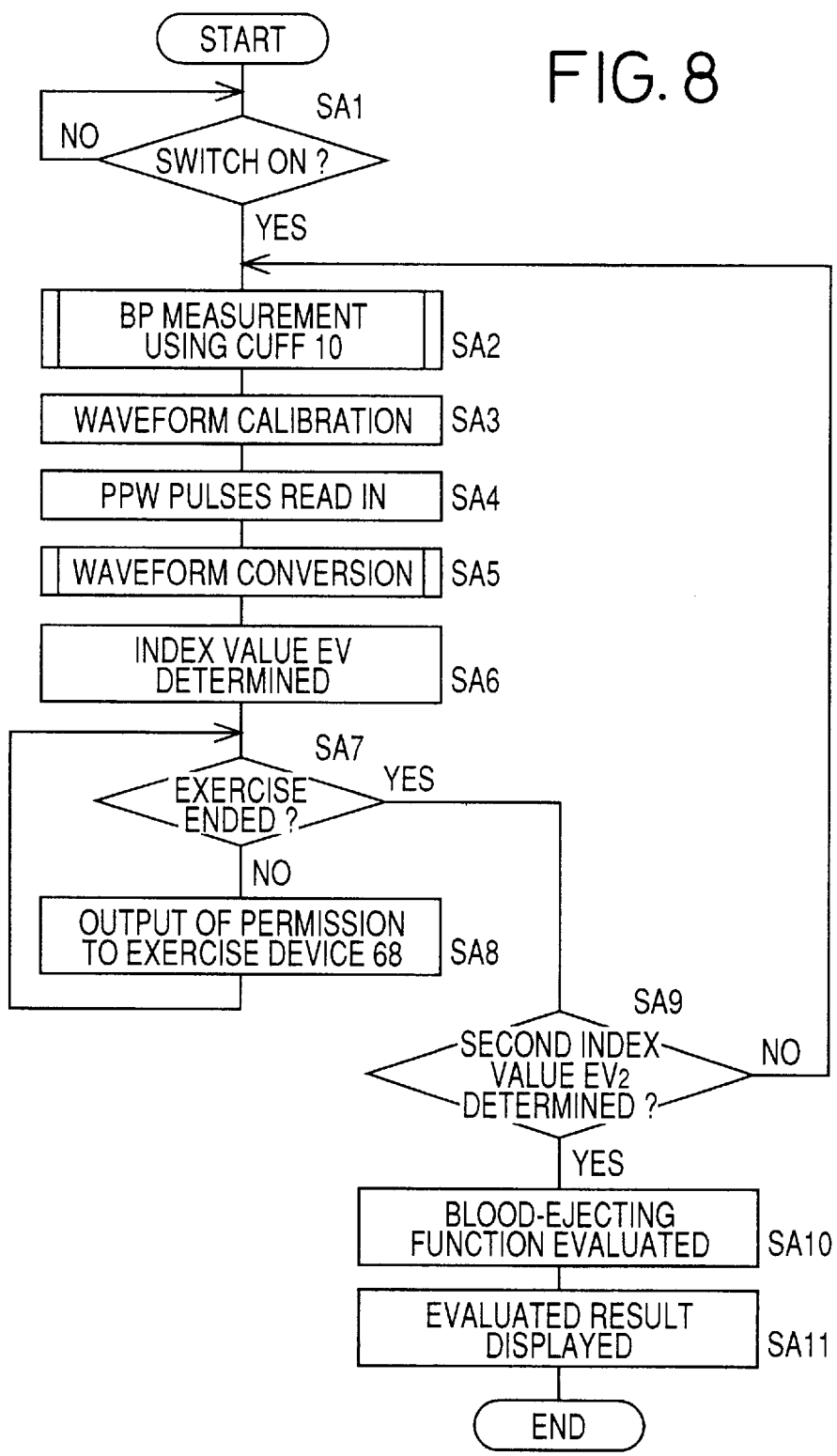
FIG. 8 is a flow chart representing a control program according to which the apparatus of FIG. 1 operates.
Figure 9:
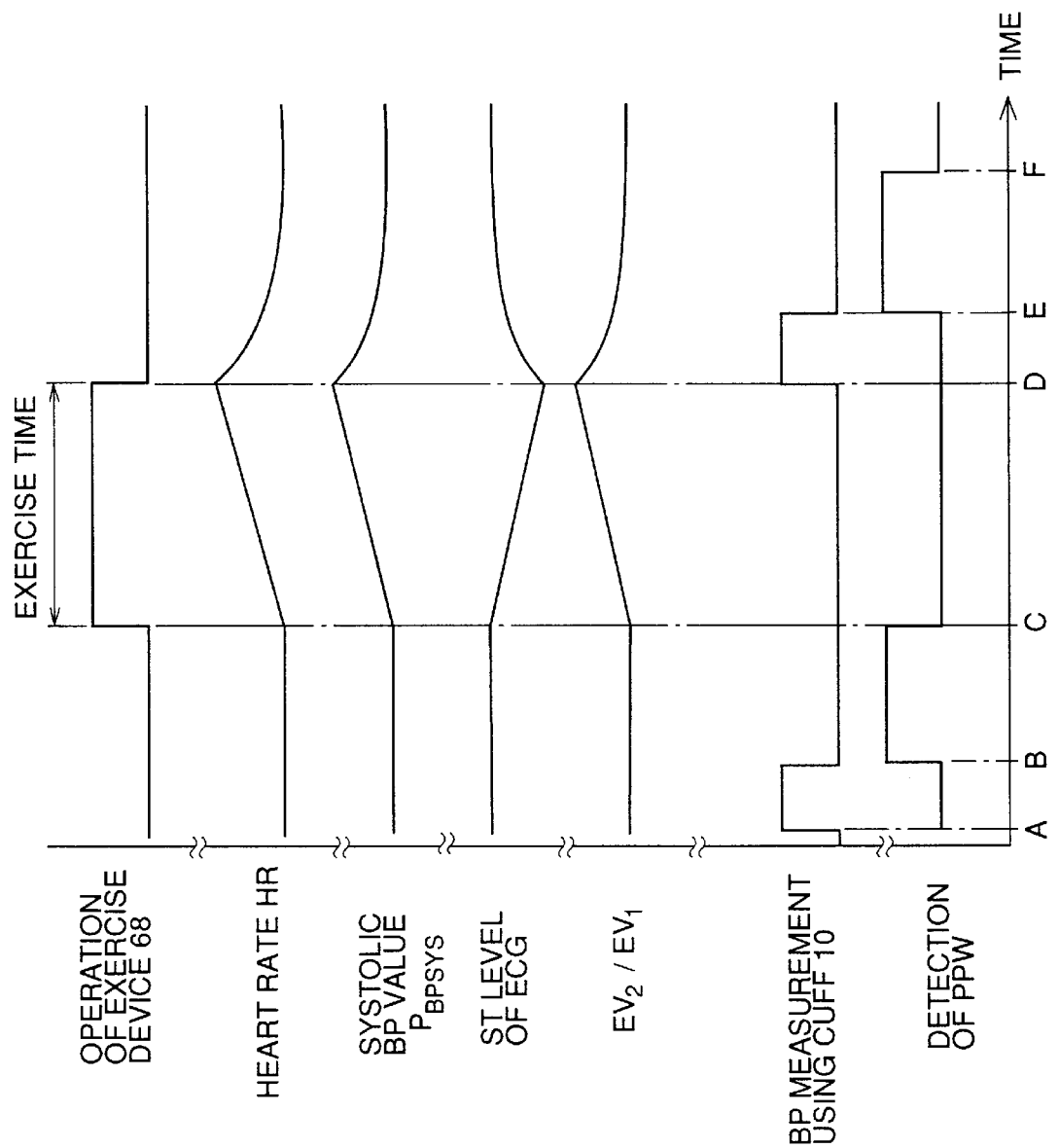
FIG. 9 is a time chart representing respective operations of an exercise device, a blood pressure ("BP") measuring device and the PPW sensor of the apparatus of FIG. 1, and respective variations of various sorts of physical information obtained from a living subject.
Figure 10:
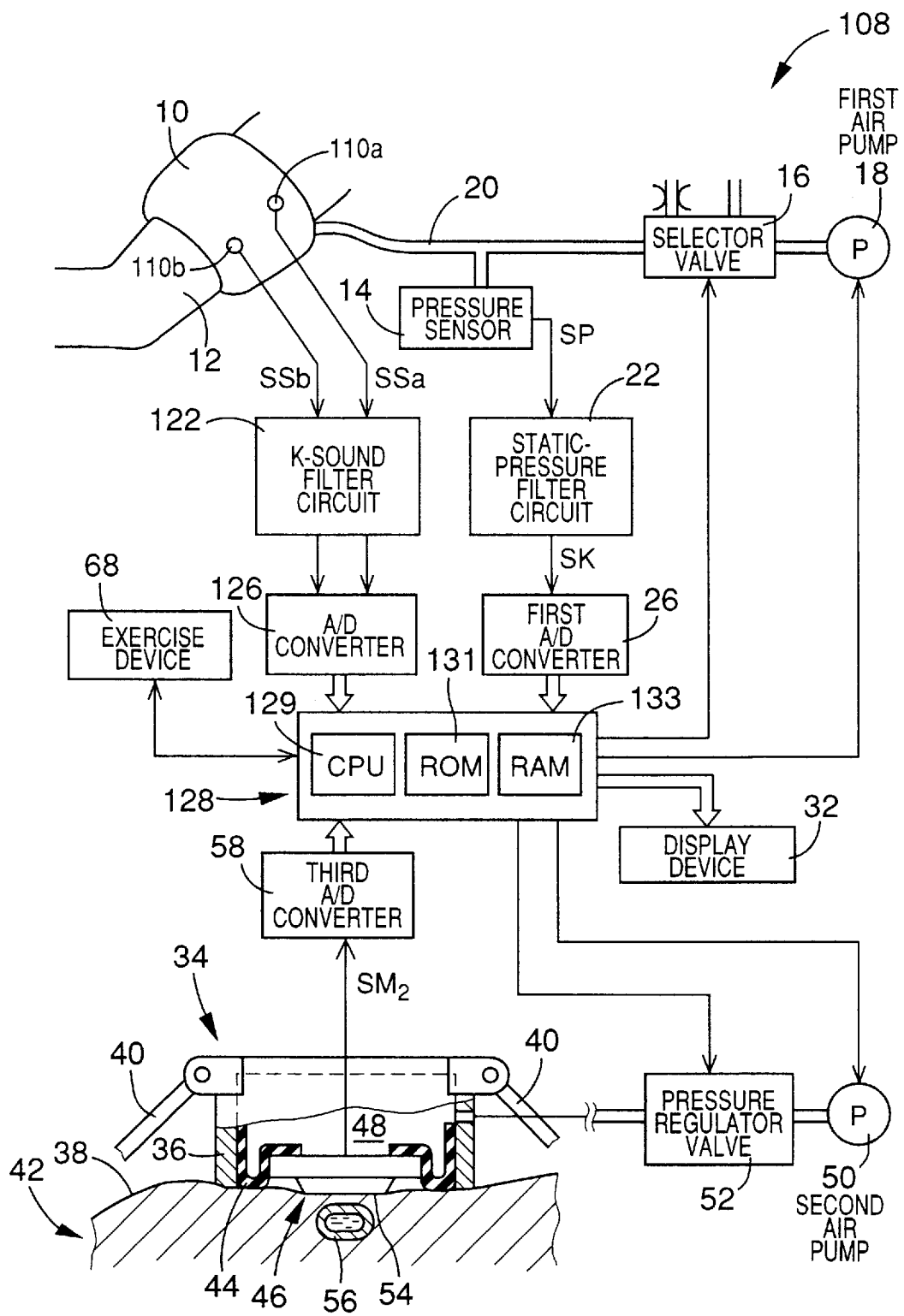
FIG. 10 is a diagrammatic view corresponding to FIG. 1, showing another BEF evaluating apparatus as a second embodiment of the present invention.

The second BEF evaluating apparatus 108 operates basically according to the same flow chart as that shown in FIG. 8. However, at Step SA2, the second apparatus 108 carries out a BP measuring routine in accordance with the flow chart of FIG. 13. A CPU 129 of the control device 128 determines a systolic and a diastolic BP value of the patient according to the control program represented by the flow chart of FIG. 13 and stored in a ROM 131, by utilizing the temporary-storage function of a RAM 133.

First, at Step SA102-1, the CPU 129 starts a first air pump 18 and switches a selector valve 16 to a first state to increase the pressure $P_k$ of the cuff 10 quickly.

Subsequently, at Step SA102-2, the CPU 129 judges whether the cuff pressure $P_k$ has been increased up to a target value $P_1$ (e.g., 180 mmHg) which is pre-determined to be sufficiently higher than an estimated systolic BP value of the patient. If a negative judgment is made at Step SA102-2, Steps SA102-1 and SA102-2 are repeated to continue to increase the cuff pressure $P_k$. Meanwhile, if a positive judgment is made, the control of the CPU 129 goes to Step S102-3 to stop the air pump 18 and switch the selector valve 16 to the second state to decrease the cuff pressure $P_k$ slowly at the rate of about 2 to 3 mmHg/sec.

Subsequently, at Step SA102-4, the CPU 129 judges whether the CPU 29 has received a K sound from each of the microphones 110a, 110b. If a negative judgment is made at Step SA102-4, Steps SA102-3 and SA102-4 are repeated. On the other hand, if a positive judgment is made at Step SA102-4, the control of the CPU 129 goes to Steps SA102-5, SA102-6, and SA102-7, i.e., BP determining algorithm. More specifically described, at Step SA102-5, the CPU 129 determines a delay time DT of the time of detection of the distal-side K sound by the distal-side microphone 110b, from that of the corresponding proximal-side K sound by the proximal-side microphone 11a. The CPU 129 determines this delay time DT by calculating the difference of the time of production of a heartbeat-synchronous pulse of the K-sound signal SSb from the time of production of a corresponding heartbeat-synchronous pulse of the K-sound signal SSa. Step SA102-5 corresponds to the delay-time determining means 161.

At Step SA102-6, the CPU 129 calculates an evaluation value, $L(P_k)$, as the product of the delay time DT determined at Step SA102-5 and a magnitude MA of the distal-side K sound detected by the distal-side microphone 110b at Step SA102-4, i.e., a magnitude of the heartbeat-synchronous pulse of the K-sound signal SSb. The CPU 129 calculates the evaluation value $L(P_k)$ for each of the distal-side K sounds which are detected by the distal-side microphone 110b during the period of slow deflation of the cuff pressure $P_k$. Thus, the CPU 129 provides an evaluation curve L connecting the calculated evaluation values $L(P_k)$, along the axis of abscissa indicative of the cuff pressure $P_k$. Step SA102-6 corresponds to the curve providing means 162.

Step SA102-6 is followed by Step SA102-7 to specify two cuff-pressure values where the curve L significantly largely changes, determines one $P_{KSYS}$ Of the two cuff-pressure values which is higher than the other, as a systolic BP value $P_{BPSYS}$ of the subject, and determines the other, lower one $P_{KDIA}$ of the two cuff-pressure values as a diastolic BP value $P_{BPDIA}$ Of the subject. Step SA102-7 corresponds to the BP-value determining means 163.

Subsequently, at Step S102-8, the CPU 129 judges whether the BP measurement has ended. If a negative judgment is made at Step SA102-8, the control of the CPU 129 goes back to Step S102-3 and the following steps. Meanwhile, if a positive judgment is made at Step SA102-8, the control of the CPU 129 goes to Step SA102-9 to switch the selector valve 16 to the third state to decrease the cuff pressure $P_k$ quickly, store the systolic and diastolic BP values $P_{BPSYS}$, $P_{BPDIA}$ in an appropriate area of the RAM 133, and control a display device 32 to display the BP values $P_{BPSYS}$, $P_{BPDIA}$ and a heart rate HR of the patient. The heart rate HR may be determined, at Step SA102-7, based on the time interval between successive two distal-side K sounds detected by the distal-side microphone 110b.

As is apparent from the foregoing description, in the second BEF evaluating apparatus 108, the delay-time determining means 161 determines the delay time DT of each of the distal-side K sounds from a corresponding one of the proximal-side K sounds, and the curve providing means 162 calculates the product of the magnitude MA of each of the distal-side K sounds and a corresponding one of the delay times DT and provides the curve L connecting the respective products, along the axis indicative of the cuff pressure $P_k$. The BP-value determining means 163 specifies two cuff-pressure values corresponding to two points on the curve L where the curve L significantly largely changes, determines one $P_{KSYS}$ of the two cuff-pressure values which is higher than the other, as a systolic BP value $P_{BPSYS}$ of the patient, and determines the other cuff-pressure value $P_{KDIA}$ as a diastolic BP value $P_{BPDIA}$ Of the patient. The thus determined systolic and diastolic BP values $P_{BPSYS}$, $P_{BPDIA}$ are used to calibrate the waveform of PPW detected by a PPW sensor 46 shown in FIG. 10.

Since the curve L is obtained by connecting the plotted points corresponding to the respective products, MA x DT, the curve L exaggeratedly changes at two cuff-pressure values corresponding to systolic and diastolic BP values of the patient. Thus, the curve L is free from noise or other adverse effects resulting from, e.g., physical motion of the patient. Thus, the present apparatus 108 measures the BP values of the patient with higher accuracy than conventional apparatus. Therefore, the present apparatus 108 evaluates the blood-ejecting function of the patient with high accuracy by utilizing the accurate BP values of the patient measured before or after the patient undergoes the physical exercise. In addition, the accuracy of diagnosis of silent myocardial ischemia is improved.

Figure 13:
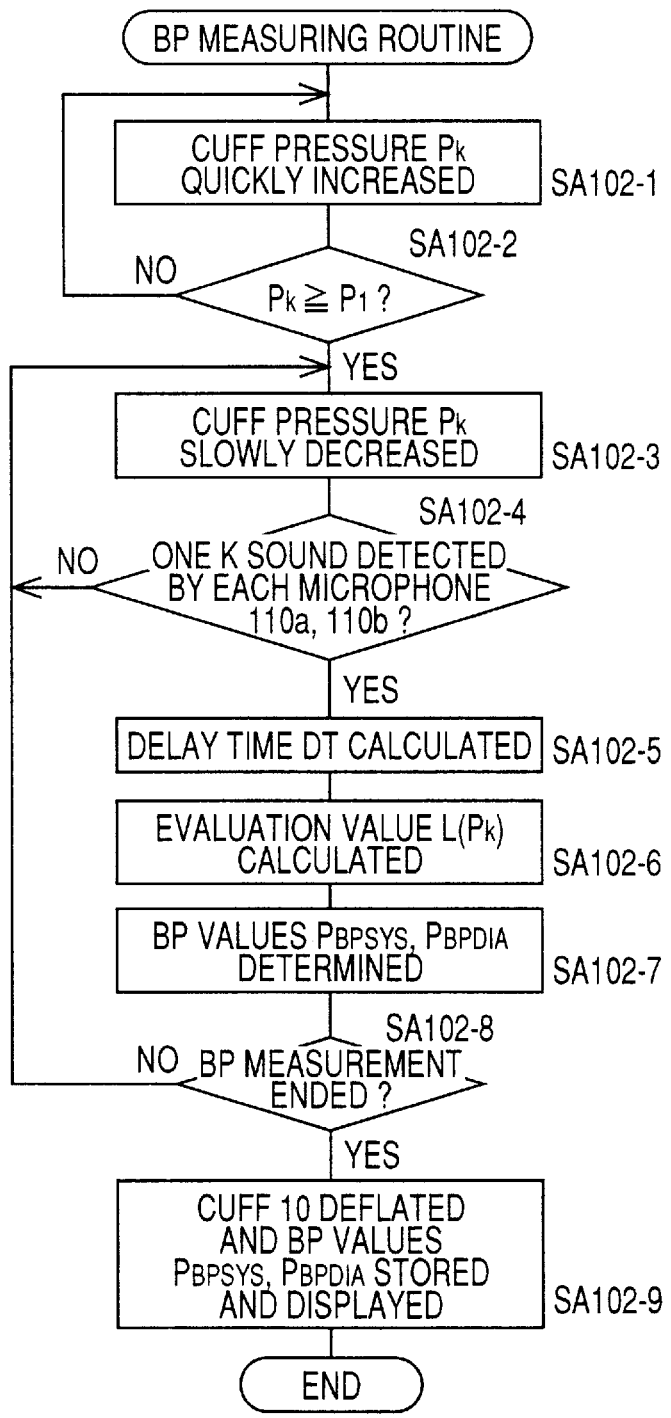
FIG. 13 is a flow chart representing a BP measuring routine according to which the apparatus of FIG. 10 operates.
Figure 14:
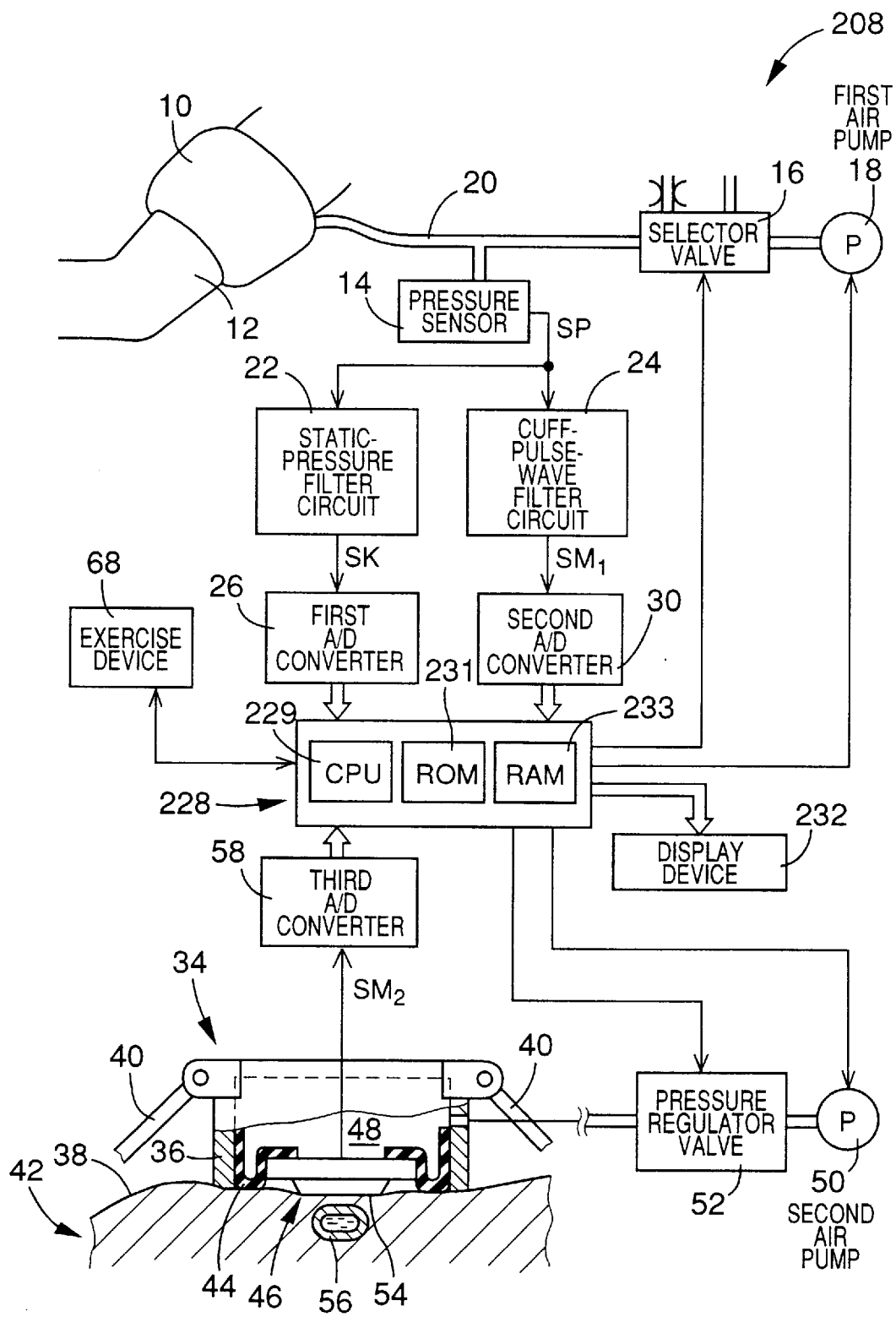
FIG. 14 is a diagrammatic view corresponding to FIG. 1, showing a cardiac-function evaluating apparatus as a third embodiment of the invention.

While at Steps SA102-3 to SA102-7 of FIG. 13 the BP values of the patient are determined based on the K sounds detected by the microphones 110a, 110b while the cuff pressure $P_k$ is slowly decreased, it is possible to determine BP values based on K sounds detected by the microphones 110a, 110b while the cuff pressure $P_k$ is slowly increased.

Referring next to FIGS. 14 to 23 there will be described a third embodiment of the present invention. The third embodiment relates to a myocardial-ischemia evaluating apparatus 208 which has basically the same hardware construction as that of the BEF evaluating apparatus 8 shown in FIG. 1 and the same BP measuring means 62 (FIG. 15) as that of the apparatus 8. However, the apparatus 208 has an electronic control device 228 including a CPU 229, a ROM 231, and a RAM 233, and a display device 232, and operates according to the control program represented by the flow chart of FIG. 19 including some steps common to the flow chart of FIG. 8. The following description only relates to the differences of the third embodiment from the first embodiment. The same reference numerals as used in the first embodiment are used to designate the corresponding elements or parts of the third embodiment, and the description of those elements or parts is omitted.

Figure 15:
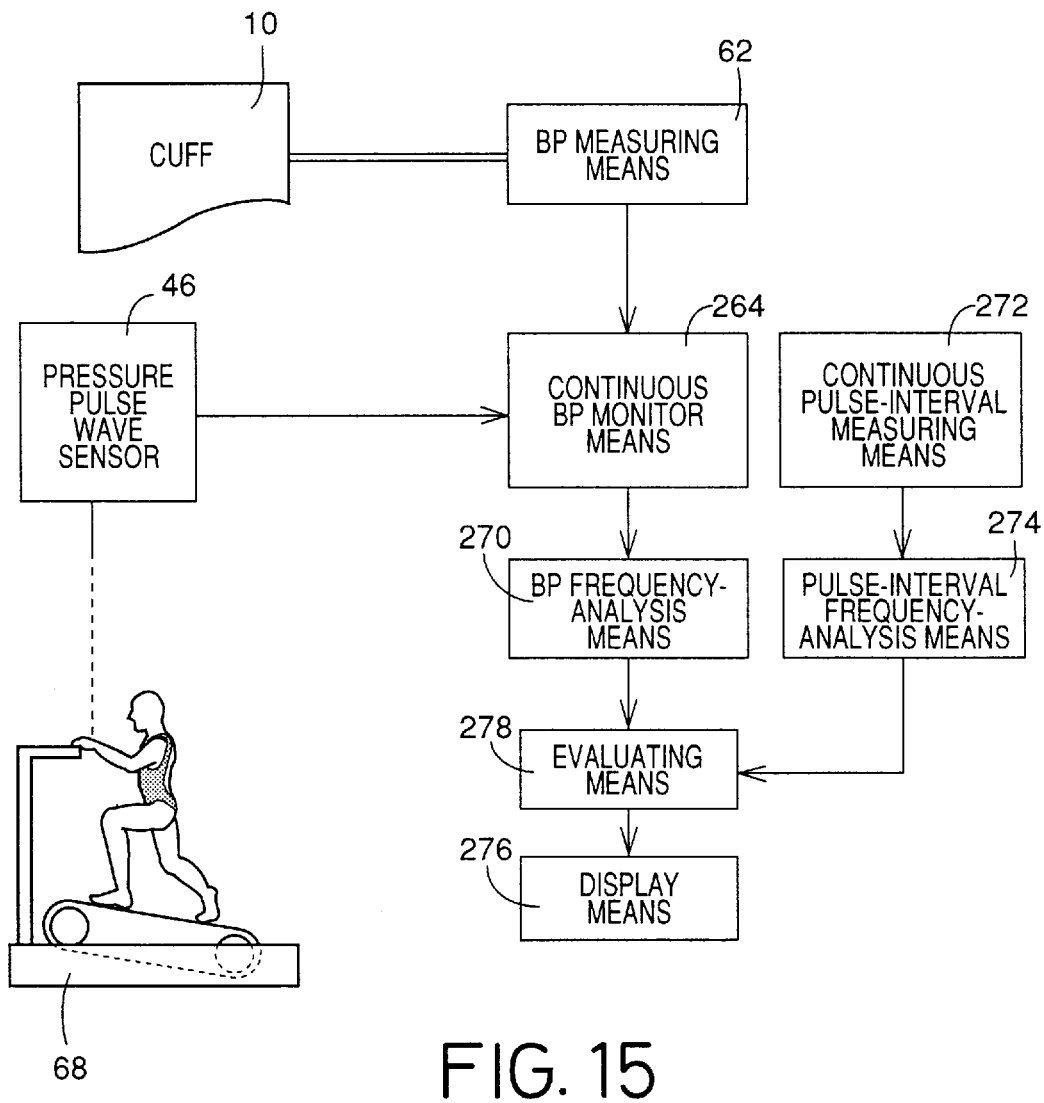
FIG. 15 is a diagrammatic view for explaining various functions of a control device of the evaluating apparatus of FIG. 14.

FIG. 15 illustrates various functions of the electronic control device 228 of the present apparatus 208. The control device 228 functions as a part of the BP measuring means 62 that is the same as the BP measuring means 62 of the first embodiment shown in FIG. 1. The control device 228 also functions as continuous BP monitor means 264 which determines a $P_{BP}$-$P_M$ relationship between BP values $P_{BP}$ and PPW magnitudes $P_M$ that is expressed by a mathematical linear function and is shown in FIG. 3, based on at least two of a first combination of an upper-peak magnitude $P_{Hpk}$ of a heartbeat-synchronous pulse of PPW detected by a PPW sensor 46 and a systolic BP value $P_{BPSYS}$ measured by the BP measuring means 62, a second combination of a mean magnitude of the same pulse and a measured mean BP value $P_{BPMEAN}$, and a third combination of a lower-peak magnitude $P_{Lpk}$ of the same pulse and a measured diastolic BP value $P_{BPDIA}$. The mean magnitude of each pulse of the PPW may be defined as a height of the center of gravity of an area defined by the waveform of that pulse. The continuous BP monitor means 264 determines a $P_{BP}$-$P_M$ relationship before and after a patient undergoes a physical exercise on an exercise device 68, and calibrates the waveform of PPW detected by the PPW sensor 46 before or after the physical exercise, according to the $P_{BP}$-$P_M$ relationship determined before or after the exercise. The calibrated waveform of the PPW represents, with high accuracy, the continuous change of blood pressure inside a radial artery 56. Thus, the upper-peak magnitude of each of the heartbeat-synchronous pulses of the calibrated waveform of the PPW represents a systolic BP value of the patient, and the lower-peak magnitude of each pulse of the calibrated waveform represents a diastolic BP value of the patient. Thus, the continuous BP monitor means 264 continuously determines, for example, the systolic BP values of the patient based on the PPW detected by the PPW sensor 46 according to the $P_{BP}$-$P_M$ relationship determined before or after the physical exercise of the patient.

Figure 22:
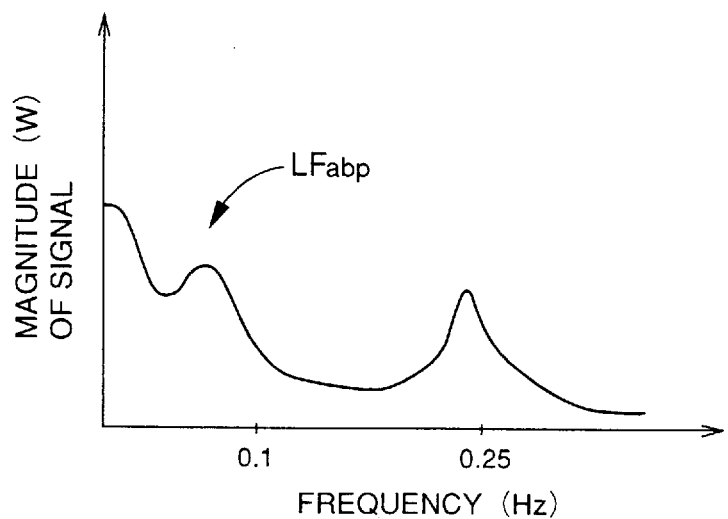
FIG. 22 is a graph showing a frequency spectrum of BP fluctuating components contained in the continuously measured BP values of the patient.

Blood-pressure frequency-analysis means 270 analyzes respective frequencies of blood-pressure (BP) fluctuating components occurring in the BP values (e.g., systolic BP values) continuously measured by the BP monitor means 264, thereby providing a frequency spectrum of the BP fluctuating components as shown in FIG. 22. The BP frequency-analysis means 270 extracts, from the continuously measured BP values, a first one, $LF_{abp}$, of the BP fluctuating components which has a low frequency lower than a frequency, RF, of a second one of the BP fluctuating components which corresponds to the respiration of the patient. The frequency of the first BP fluctuating component $LF_{abp}$ is about one third of the frequency RF of the second BP fluctuating component. Providing that the frequency RF is about 0.25 Hz, for example, the frequency of the first fluctuating component $LF_{abp}$ has a peak at about 0.07 Hz.

The control device 228 also functions as a part of continuous pulse-interval measuring means 272 which continuously measures a time interval, RR, between respective upper peaks of each pair of successive two pulses of a plurality of heartbeat-synchronous pulses of the calibrated waveform provided by the continuous BP monitor means 264 or the waveform of the PPW detected by the PPW sensor 46, thereby providing continuously measured pulse-interval values RR of the patient before or after the physical exercise of the patient.

Figure 23:
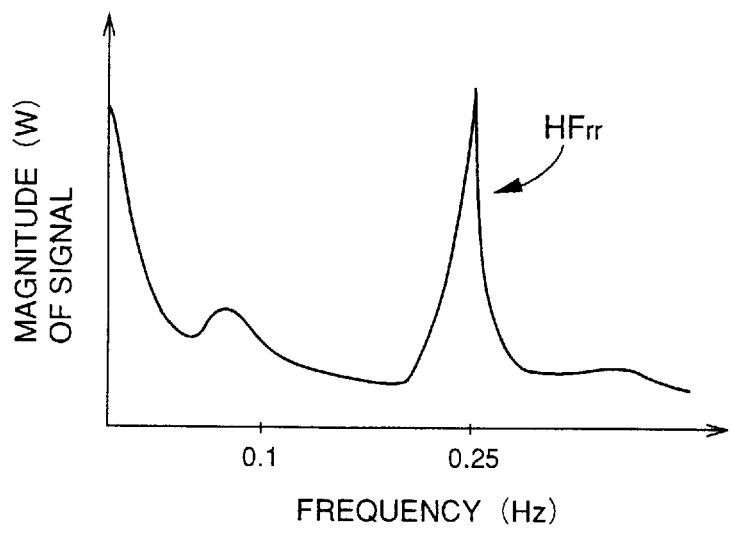
FIG. 23 is a graph showing a frequency spectrum of pulse-interval fluctuating components contained in the continuously measured pulse-interval values of the patient.
Figure 24:
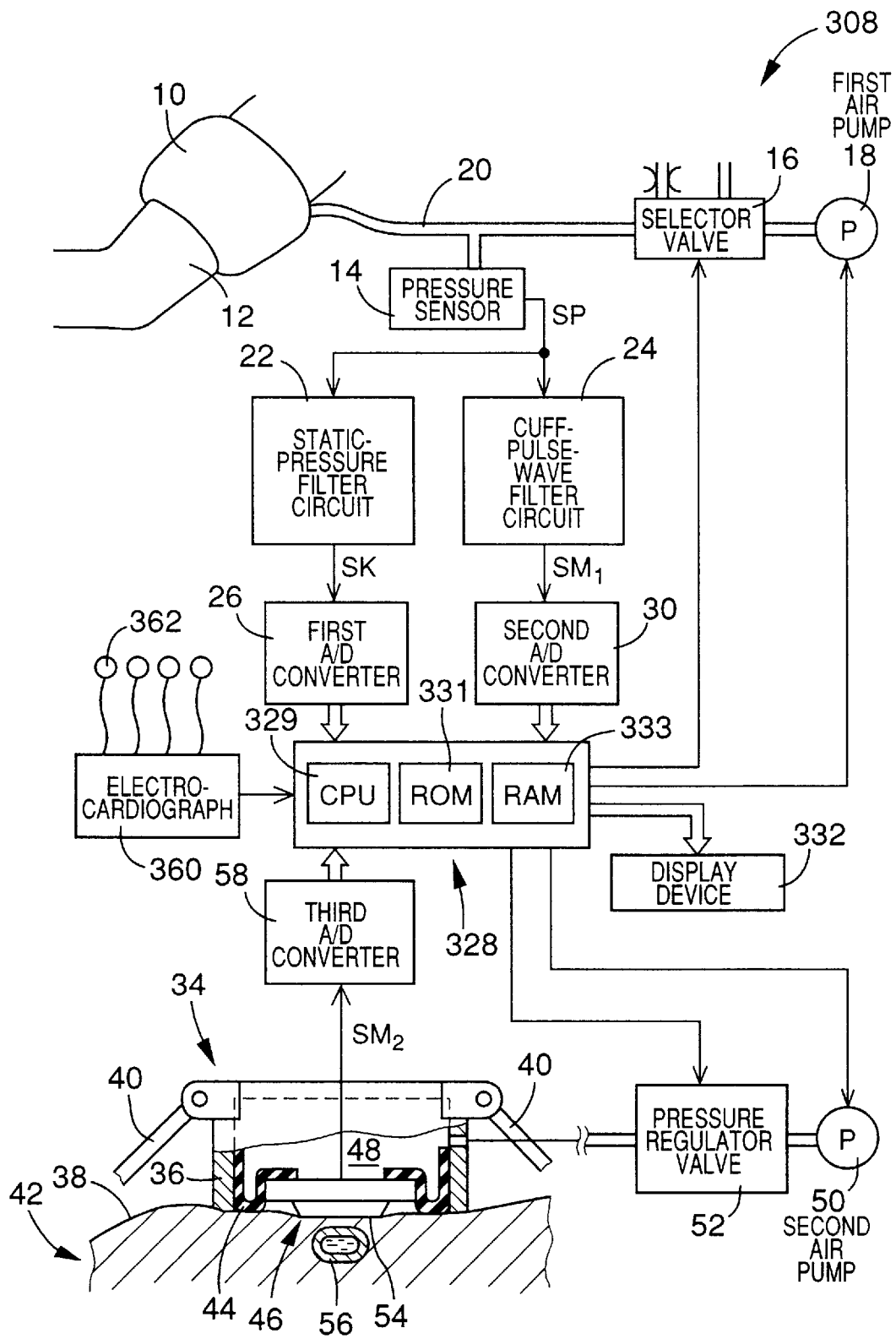
FIG. 24 is a diagrammatic view corresponding to FIG. 1, showing a BP monitor apparatus which also functions as a cardiac-function evaluating apparatus as a fourth embodiment of the invention.

Pulse-interval frequency-analysis means 274 analyzes respective frequencies of pulse-interval fluctuating components occurring in the pulse-interval values RR continuously measured by the continuous pulse-interval measuring means 272, thereby providing a frequency spectrum of the pulse-interval fluctuating components as shown in FIG. 23. The pulse-interval frequency-analysis means 274 extracts, from the continuously measured pulse-interval values RR, one, $HF_{rr}$, of the pulse-interval fluctuating components which has a high frequency substantially equal to the frequency RF of the second BP fluctuating component which corresponds to the respiration of the patient.

Figure 16:
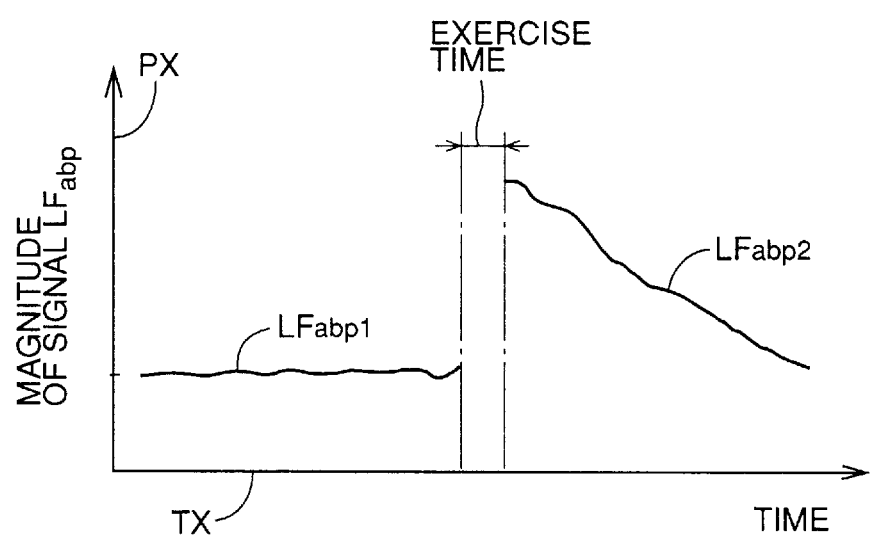
FIG. 16 is a view of a screen image of a display device of the apparatus of FIG. 14 showing a time-wise change of low-frequency BP fluctuating component $LF_{abp}$ obtained after the physical exercise of a patient, in comparison with a time-wise change of the fluctuating component $LF_{abp}$ obtained before the exercise.
Figure 17:
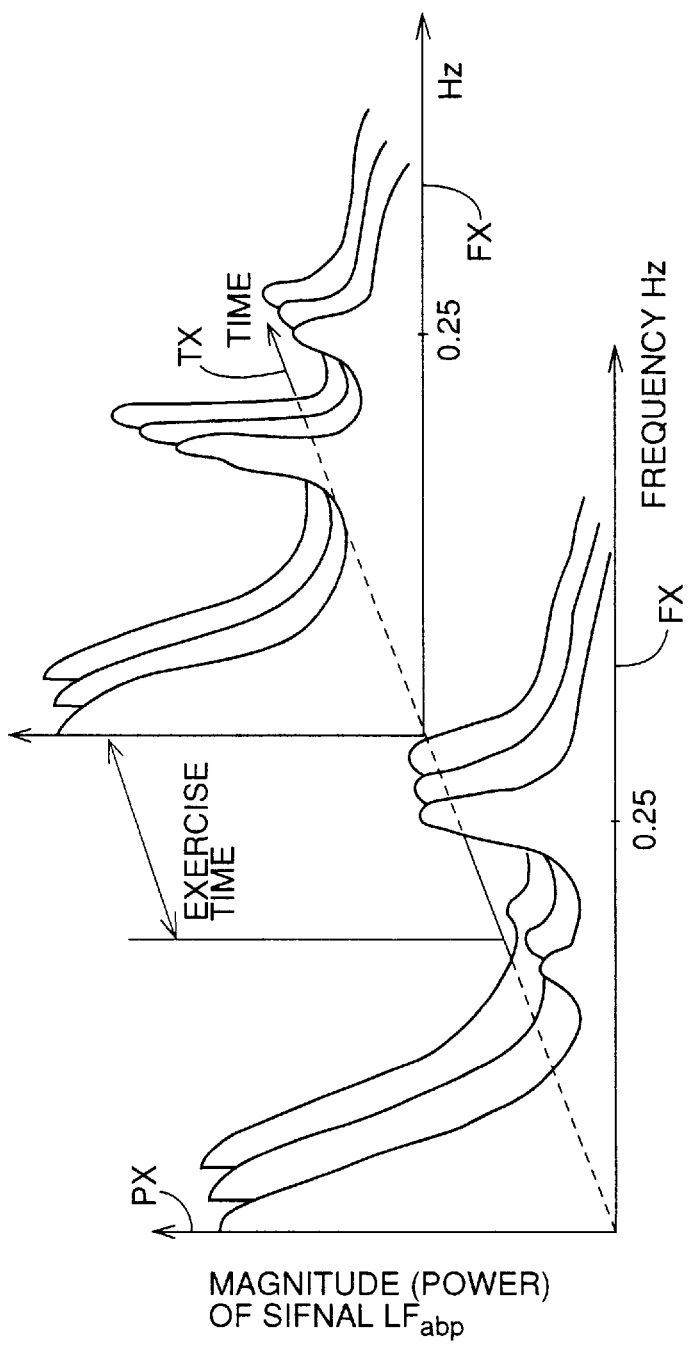
FIG. 17 is a view of another screen image of the display device showing a three-dimensional representation of a frequency spectrum of BP fluctuating components contained in the BP values measured after the exercise, in comparison with a three-dimensional representation of a frequency spectrum of BP fluctuating components contained in the BP values measured before the exercise, thereby showing a time-wise change of low-frequency BP fluctuating component $LF_{abp}$ obtained after the exercise of the patient, in comparison with a time-wise change of the fluctuating component $LF_{abp}$ obtained before the exercise.
Figure 18:
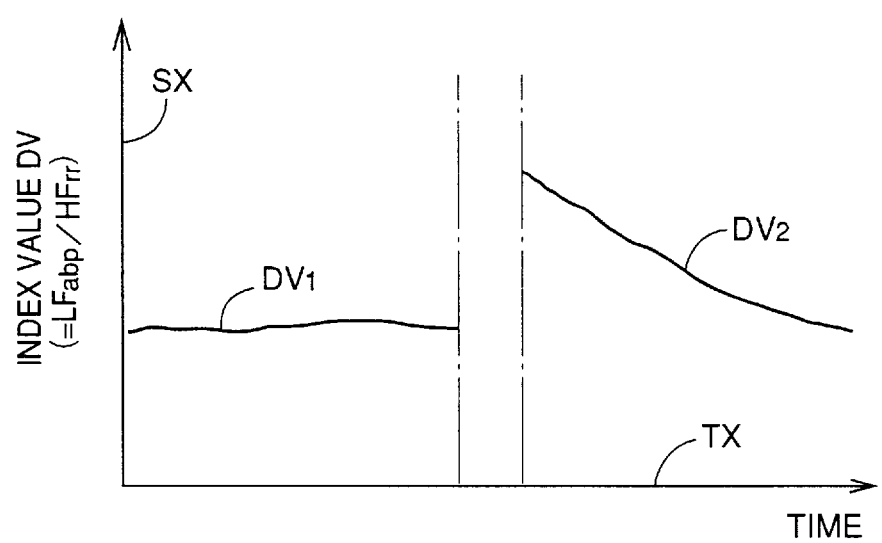
FIG. 18 is a view of yet another screen image of the display device showing a second index value $DV_2$ obtained after the exercise, in comparison with a first index value $DV_1$ obtained before the exercise, thereby showing a time-wise change of low-frequency BP fluctuating component $LF_{abp}$ obtained after the exercise, in comparison with a time-wise change of the fluctuating component $LF_{abp}$ obtained before the exercise.

Display means 276 controls the display device 232 to display, on a screen thereof, (a1) a low-frequency BP fluctuating component, $LF_{abp1}$, extracted from the continuously measured BP values provided by the BP monitor means 264 before the patient undergoes a physical exercise on the exercise device 68 and/or (a2) a first index value, $DV_1$, of an index DV determined based on the low-frequency BP fluctuating component $LF_{abp1}$ obtained before the exercise, in comparison with (b1) a low-frequency BP fluctuating component, $LF_{abp2}$, extracted from the continuously measured BP values provided by the BP measuring means 264 after the subject undergoes the physical exercise and/or (b2) a second index value, $DV_2$, of the index DV determined based on the low-frequency BP fluctuating component $LF_{abp2}$ obtained after the exercise. Thus, an observer can compare the fluctuating component $LF_{abp1}$ and/or the index value $DV_1$ and the fluctuating component $LF_{abp2}$ and/or the index value $DV_2$, with each other, on the screen of the display device 232. FIGS. 16, 17 and 18 shows examples of physical information displayed by the display device 232.

FIG. 16 shows a graph representing a time-wise change of the fluctuating component or signal $LF_{abp1}$ and a time-wise change of the fluctuating component or signal $LF_{abp2}$, in a two-dimensional system defined by a first axis, TX, indicative of time and a second axis, PX, indicative of magnitude of the fluctuating component $LF_{abp}$. FIG. 17 shows a graph representing frequency spectrums of the BP fluctuating components or signals $LF_{abp1}$ obtained before the exercise, and frequency spectrums of the BP fluctuating components or signals $LF_{abp2}$ obtained after the exercise, in a three-dimensional system defined by the first and second axes TX, PX and a third axis, FX, indicative of frequency. FIG. 18 shows a time-wise change of first index values $DV_1$ determined based on the fluctuating component or signal $LF_{abp1}$ and a time-wise change of second index values $DV_2$ determined based on the fluctuating component or signal $LF_{abp2}$, in a two-dimensional system defined by the first axis TX indicative of time and a second axis, SX, indicative of magnitude of index value DV. The index DV may be a ratio, $LF_{abp}/HF_{rr}$, of the magnitude of the low-frequency BP fluctuating component or signal $LF_{abp}$ to that of the high-frequency pulse-interval fluctuating component or signal $HF_{rr}$.

Evaluating means 278 automatically evaluates the myocardial ischemia of the subject based on (a1) the low-frequency BP fluctuating component $LF_{abp1}$ extracted from the continuously measured BP values provided by the BP measuring means 264 before the patient undergoes the exercise and/or (a2) the first index value $DV_1$ (=$LF_{abp1}$/$HF_{rr1}$) determined based on the low-frequency BP fluctuating component $LF_{abp1}$, and (b1) the low-frequency BP fluctuating component $LF_{abp2}$ extracted from the continuously measured BP values provided by the BP measuring means 264 after the subject undergoes the exercise and/or (b2) the second index value $DV_2$ (=$LF_{abp2}/HF_{rr2}$) determined based on the low-frequency BP fluctuating component $LF_{abp2}$. For example, the evaluating means 278 evaluates myocardial ischemia by judging whether an amount of change, $\Delta LF_{abp}$ (=$LF_{abp2}-LF_{abp1}$), of the magnitude of the fluctuating component $LF_{abp2}$ from that of the fluctuating component $LF_{abp1}$, an amount of change, $\Delta DV$ (=$DV_2-DV_1$), a rate of change, $LF_{abp2}/LF_{abp1}$, or a rate of change, $DV_2/DV_1$, is greater than a first, a second, a third, or a fourth reference value. Otherwise, the evaluating means 278 evaluates myocardial ischemia by judging whether a time of recovering of the magnitudes of the fluctuating component $LF_{abp2}$ or the second index values $DV_2$ back to a magnitude or value substantially equal to the magnitude of the fluctuating component $LF_{abp1}$ or the first index value $DV_1$, or a rate of recovering of the magnitudes of the fluctuating component $LF_{abp2}$ or the second index values $DV_2$ back to a magnitude or value substantially equal to the magnitude of the fluctuating component $LF_{abp1}$ or the first index value $DV_1$, is greater than a fifth or a sixth reference value.

Figure 19:
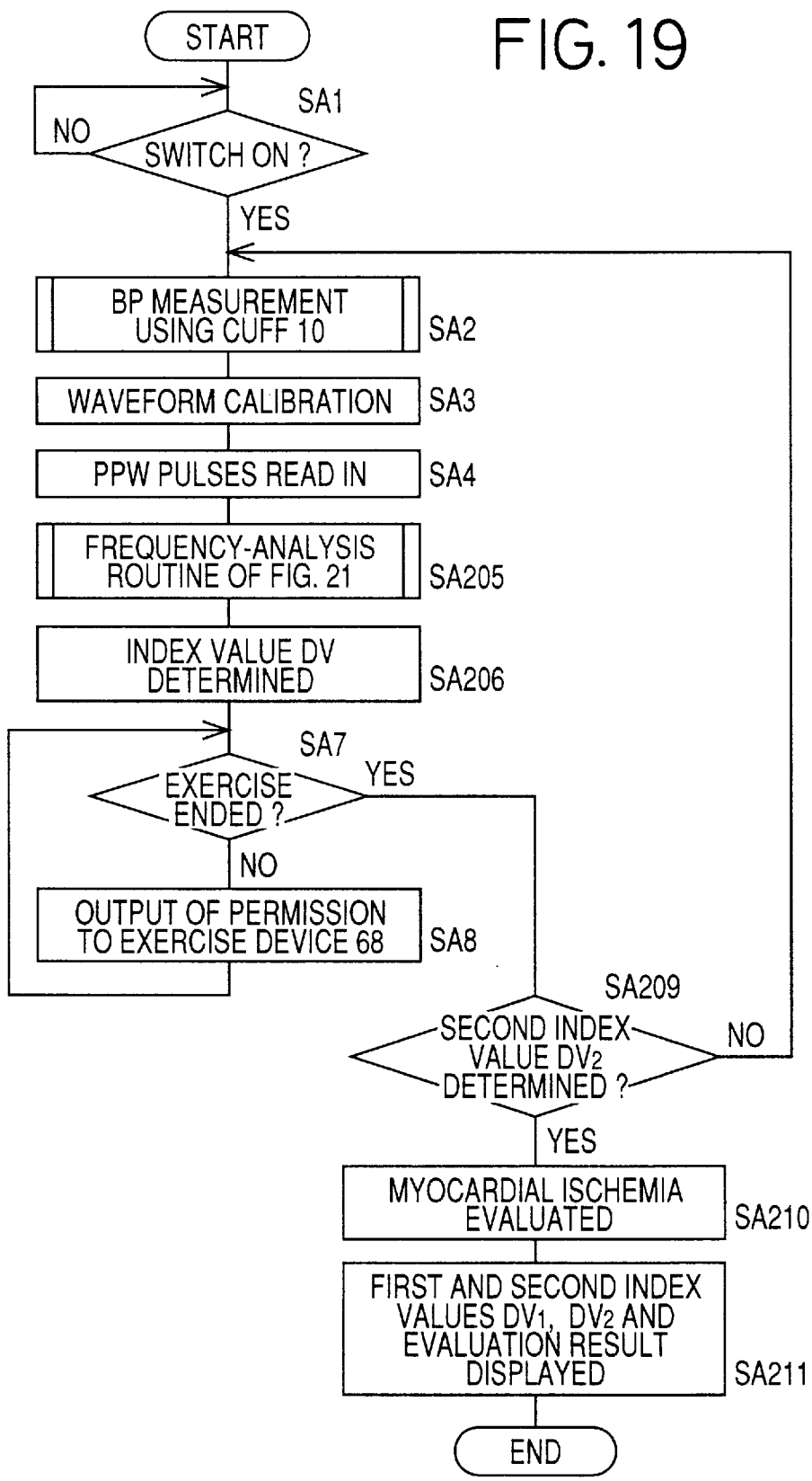
FIG. 19 is a flow chart representing a control program according to which the apparatus of FIG. 14 operates.

Next, there will be described the operation of the myocardial-ischemia evaluating apparatus 208 constructed as described above, by reference to the flow charts of FIGS. 19 and 21. Steps SA1 to SA4, SA7, SA8 of FIG. 19 are the same as those of FIG. 8, and the description thereof is omitted. The CPU 229 of the control device 228 processes input signals SK, $SM_1$, $SM_2$ according to the control programs represented by the flow charts of FIGS. 19 and 21 and pre-stored in the ROM 231, by utilizing the temporary-storage function of the RAM 233.

Figure 21:
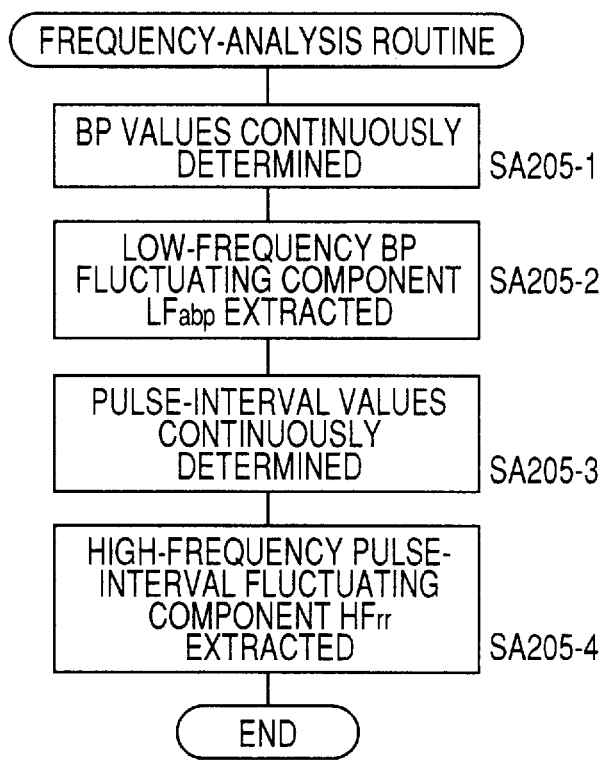
FIG. 21 is a flow chart representing a frequency-analysis routine of the control program of FIG. 19.

At Step SA205, the CPU 229 of the control device 228 carries out a frequency-analysis routine represented by the flow chart of FIG. 21. Step SA205 corresponds to the BP frequency-analysis means 270 and the pulse-interval frequency-analysis means 272.

First, at Step SA205-1, the CPU 229 calibrates, according to the $P_{BP}$-$P_M$ relationship determined at Step SA3, the waveform of each of heartbeat-synchronous pulses of the PPW read in at Step SA4 from the PPW sensor 46, and continuously determines BP values of the patient from the calibrated waveform. For example, the CPU 229 continuously determines systolic BP values of the patient from successive upper peaks of the calibrated waveform of the PPW. Step SA205-1 corresponds to the continuous BP measuring means 264.

Subsequently, at Step SA205-2, the CPU 229 analyzes respective frequencies of BP fluctuating components occurring in the systolic BP values continuously measured by the BP monitor means 264, thereby providing a frequency spectrum of the BP fluctuating components as shown in FIG. 22. In addition, the CPU 229 extracts, from the continuously measured systolic BP values, a BP low-frequency fluctuating component or signal $LF_{abp}$ having a low frequency lower than a frequency RF of a different BP fluctuating component which corresponds to the respiration of a patient. The frequency of the BP low-frequency fluctuating component $LF_{abp}$ is about one third of the frequency RF of the second BP fluctuating component. Step SA205-2 corresponds to the BP frequency-analysis means 270.

At Step SA205-3, the CPU 229 continuously measures a time interval ("pulse interval") RR between respective upper (or lower) peaks of each pair of successive two pulses of a plurality of heartbeat-synchronous pulses of the calibrated waveform provided by the continuous BP monitor means 264 at Step SA205-1 or the waveform of PPW detected by the PPW sensor 46, thereby providing continuously measured pulse-interval values RR of the patient. Step SA205-3 corresponds to the continuous pulse-interval measuring means 272.

At Step SA205-4, the CPU 229 analyzes respective frequencies of pulse-interval fluctuating components occurring in the pulse-interval values RR continuously measured by the continuous pulse-interval measuring means 272, thereby providing a frequency spectrum of the pulse-interval fluctuating components as shown in FIG. 23. In addition, the CPU 229 extracts, from the continuously measured pulse-interval values RR, a high-frequency pulse-interval fluctuating component or signal $HF_{rr}$ having a frequency substantially equal to the frequency RF of the second BP fluctuating component corresponding to the respiration of the patient. Step SA205-4 corresponds to the pulse-interval frequency-analysis means 274. Thus, the subroutine of FIG. 21 ends.

After the low-frequency BP fluctuating component or signal $LF_{abp}$ and the high-frequency pulse-interval fluctuating component or signal $HF_{rr}$ are extracted at Step SA205, the control of the CPU 229 goes to Step SA206 (FIG. 19) to determine an index value DV by dividing the magnitude of the BP fluctuating signal $LF_{abp}$ by the magnitude of the pulse-interval fluctuating signal $HF_{rr}$. This index value DV is a first index value $DV_1$ (=$LF_{abp1}/HF_{rr1}$) corresponding to the condition of patient's heart before the patient undergoes a physical exercise on the exercise device 68. Then, the control of the CPU 229 goes to Steps SA7 and SA8.

While Steps SA7 and SA8 are repeated, a positive judgment is made at Step SA7, if a prescribed physical exercise ended on the exercise device 68. In this case, Step SA7 is followed by Step SA209 to judge whether a second index value $DV_2$ has been determined. While negative judgments are made at Step SA209, the control of the CPU 229 goes back to Step SA2 to carry out another BP measurement using the cuff 10. This corresponds to the time interval from point "D" to point "E" shown in FIG. 20. Subsequently, Steps SA3, SA4 and SA205 are carried out to read in the PPW detected by the PPW sensor 46 after the physical exercise and calibrate the waveform of the thus read PPW. Moreover, at Step SA206, the CPU 229 determines an index value DV based on the BP fluctuating signal $LF_{abp}$ and the pulse-interval fluctuating signal $HF_{rr}$ obtained after the physical exercise, in the same manner as that used to determine the first index value $DV_1$. The thus determined index value DV is the second index value $DV_2$.

Once the physical exercise ends and the second index value $DV_2$ is determined, a positive judgment is made at each of Steps SA7 and SA209. This corresponds to point "F" shown in FIG. 20. Then, the control of the CPU 229 goes to Step SA210 to identify myocardial ischemia on the heart of the patient based on a change of the second index value $DV_2$ relative to the first index value $DV_1$. For example, the CPU 229 may determine a plurality of index values DV in a predetermined interval before the physical exercise, and may determine an average of those index values DV as the first index value $DV_1$. Similarly, the CPU 229 may determine a plurality of index values DV in a predetermined interval after the exercise, and may determine an average of those index values DV as the second index value $DV_2$. In this case, the CPU 229 judges that the patient is normal, if an amount of change $\Delta$ DV (=$DV_2$–$DV_1$) or a rate of change $DV_2/DV_1$ is greater than a predetermined first or second reference value, respectively, and judges that the patient is suspected to have myocardial ischemia, if the amount of change $\Delta$ DV or the rate of change $DV_1/DV_2$ is not greater than the first or second reference value, respectively. Otherwise, the CPU 229 may be adapted to judge that the patient is normal, if the recovering time TR of the second index values $DV_2$ determined after the exercise, back to a value equal to the first index time $DV_1$ is shorter than a predetermined reference value, or if the rate of recovering (i.e., slope) $\Delta DV_2$ of the second index values $DV_2$ determined after the exercise is greater than a predetermined reference value. If the activity of heart muscle of the patient is normal, the low-frequency BP fluctuating signal $LF_{abp}$ increases because of the physical exercise and, after the exercise, it quickly restores to its resting condition before the exercise. Step SA210 corresponds to the evaluating means 274.

Step SA210 is followed by Step SA211 to control the display device 232 to display, on the screen thereof, the result of evaluation of the activity of heart muscle of the patient carried out at Step SA210, and the various graphical representations shown in FIGS. 16 to 18. From those representations, the medical staff can easily grasp the respective changes of the low-frequency BP fluctuating component $LF_{abp2}$ and the second index values $DV_2$ obtained after the exercise, from the fluctuating component $LF_{abp1}$ and the first index values $DV_1$ obtained before the same. Step SA211 corresponds to the display means 276.

As is apparent from the foregoing description, in the evaluating apparatus 208, the BP frequency-analysis means 270 extracts, from the BP values continuously determined by the continuous BP monitor means 264, the low-frequency BP fluctuating component or signal $LF_{abp}$ whose frequency peak is lower than the respiration frequency RF of the patient, and the display device 232 displays the low-frequency BP fluctuating signal $LF_{abp1}$ and/or the first index value $DV_1$ obtained before the physical exercise of the patient, and the low-frequency BP fluctuating signal $LF_{abp2}$ and/or the second index value $DV_2$ obtained after the physical exercise, in such a manner that an observer can compare the fluctuating signal $LF_{abp1}$ and/or index value $DV_1$ and the fluctuating signal $LF_{abp2}$ and/or the index value $DV_2$, with each other. Thus, a doctor can easily grasp the change of the fluctuating signal $LF_{abp2}$ and/or the index value $DV_2$ from the fluctuating signal $LF_{abp1}$ and/or index value $DV_1$ and accordingly can non-invasively judge whether the patient has myocardial ischemia or not. Since the low-frequency BP fluctuating signal $LF_{abp}$ directly corresponds to the activity of vasomotor sympathetic nerve of the patient, the present apparatus 208 can evaluate or identify silent myocardial ischemia with higher accuracy than in the case where ECG or change of heart rate HR that contains various fluctuating components is used for the same purpose.

Since the third apparatus 208 automatically evaluates the activity of heart muscle of the patient based on the low-frequency BP fluctuating signals $LF_{abp1}$, $LF_{abp2}$ obtained before and after the patient undergoes the predetermined exercise, medical staff can easily use the apparatus 208 and evaluate the cardiac blood-ejecting function of the patient.

The third apparatus 208 employs the continuous pulse-interval measuring means 272 which continuously measures the pulse-interval values RR of the patient, and the pulse-interval frequency-analysis means 274 which extracts, from the pulse-interval values RR, the high-frequency pulse-interval fluctuating component or signal $HF_{rr}$ whose frequency peak is substantially equal to the respiration frequency RF of the patient. The evaluating means 278 determines, as the index DV, the ratio of the magnitude of signal $LF_{abp}$ to that of signal $HF_{rr}$. This index DV is more reliable for evaluating the condition of patient's heart than the low-frequency BP fluctuating signal $LF_{abp}$ only.

In the case where the evaluating means 278 evaluates the myocardial ischemia of the patient by judging whether the amount or rate of change of the second index value $DV_2$ from the first index value $DV_1$ is greater than a predetermined first or second reference value, it does not need a complex algorithm.

Meanwhile, in the case where the evaluating means 278 evaluates myocardial ischemia based on the time of recovering TR of the second index values $DV_2$ back to a value equal to the first index value $DV_1$, or the rate of change of the second index values $DV_2$, the ischemia can be identified with higher accuracy.

In the third apparatus 208, the continuous BP monitor means 264 continuously determines systolic BP values of the patient based on respective upper-peak magnitudes of the heartbeat-synchronous pulses of the PPW detected by the PPW sensor 46, and the BP frequency-analysis means 270 extracts, from the systolic BP values corresponding to the heartbeat-synchronous pulses, the low-frequency BP fluctuating component or signal $LF_{abp}$. Thus, the signal $LF_{abp}$ enjoys high accuracy.

While in the third embodiment both the evaluating means 278 and the display means 276 are employed, it is possible to omit one of the two means 278, 276.

Although in the third embodiment the PPW sensor 46 is worn on a wrist of the patient to detect a PPW from the radial artery 56, it is possible to wear the PPW sensor 46 on an ankle or the neck of the patient to detect a PPW from a dorsal pedal artery or a carotid artery of the patient.

While the third apparatus 208 employs the continuous BP monitor means 264 which calibrates the waveform of PPW detected by the PPW sensor 46 according to the $P_{BP}$-$P_M$ relationship determined before or after the exercise of the patient, and provides a continuous waveform representing the actual blood pressure inside the radial artery 56, it is not necessary to calibrate the waveform of PPW detected by the PPW 46, so long as the conditions under which the PPW is detected by the PPW sensor 46 are not changed so much between before and after patient's exercise. The frequency analysis of fluctuating components of BP values does not need so highly accurate data.

Figure 20:
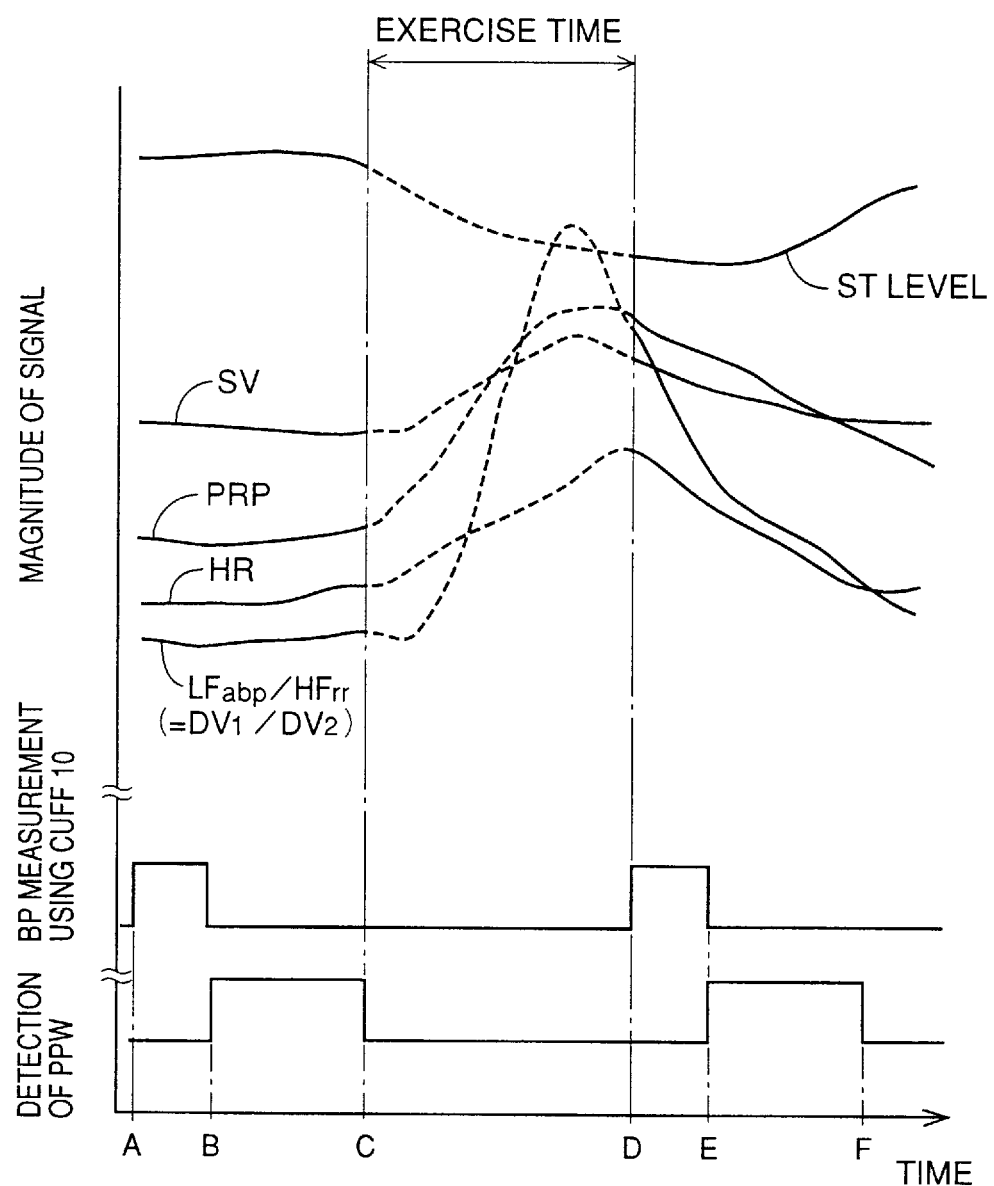
FIG. 20 is a time chart representing respective operations of a BP measuring device using a cuff and a pressure pulse wave sensor of the apparatus of FIG. 14, and respective changes of various sorts of physical information obtained from the patient.

FIG. 20 shows, in addition to a curve representing a time-wise change of the index DV ($=LF_{abp}/HF_{rr}$), a curve representing a time-wise change of the ST level of ECG, a curve representing a time-wise change of the area SV (stroke volume) defined by the calibrated waveform within the left ventricular ejection time ET (=LVET) starting with the rising point and ending with the notch DN, a curve representing a time-wise change of the pressure rate product, PRP, obtained as the product of blood pressure BP and heart rate HR, and a curve representing a time-wise change of the heart rate HR, each along a common time axis including intervals before and after the exercise of the patient. In this case, the third apparatus 208 additionally employs an electrocardiograph which produces ECG, means for calculating the ST levels of the ECG, and means for calculating the pressure rate products PRP. The ST level of ECG is the average height of ECG signal between the S wave and the T wave of each heartbeat-synchronous pulse.

In the case where an electrocardiograph is employed, the continuous pulse-interval measuring means 272 may be adapted to measure pulse-interval values RR based on the waveform of ECG, e.g., continuously measure a time interval (i.e., RR interval) between respective R waves of each pair of successive two pulses of the waveform of ECG.

Referring next to FIGS. 24 to 29, there will be described a BP monitor apparatus 308 which also functions as a cardiac function evaluating apparatus as a fourth embodiment of the present invention. The BP monitor apparatus 308 has basically the same hardware construction as that of the BEF evaluating apparatus 8 shown in FIG. 1 and the same BP measuring means 62 (FIG. 25) as that of the apparatus of FIG. 8. However, the apparatus 308 includes an electronic control device 328 including a CPU 329, a ROM 331, and a RAM 333, a display device 332, and an electrocardiograph 360, and operates according to the control program represented by the flow chart of FIG. 28 including some steps common to the flow chart of FIG. 8. The following description only relates to the differences of the fourth embodiment from the first embodiment. The same reference numerals as used in the first embodiment are used to designate the corresponding elements or parts of the fourth embodiment, and the description of those elements or parts is omitted.

The electrocardiograph 360 includes a plurality of electrodes 362 which are adapted to be attached to prescribed positions on a patient and through which the cardiograph 360 detects a time-wise change of electric potential of the heart muscle of the patient and produces an electric signal representing the detected change, i.e., electrocardiogram ("ECG"). The electric signal representing the ECG is supplied to the electronic control device 328.

Figure 25:
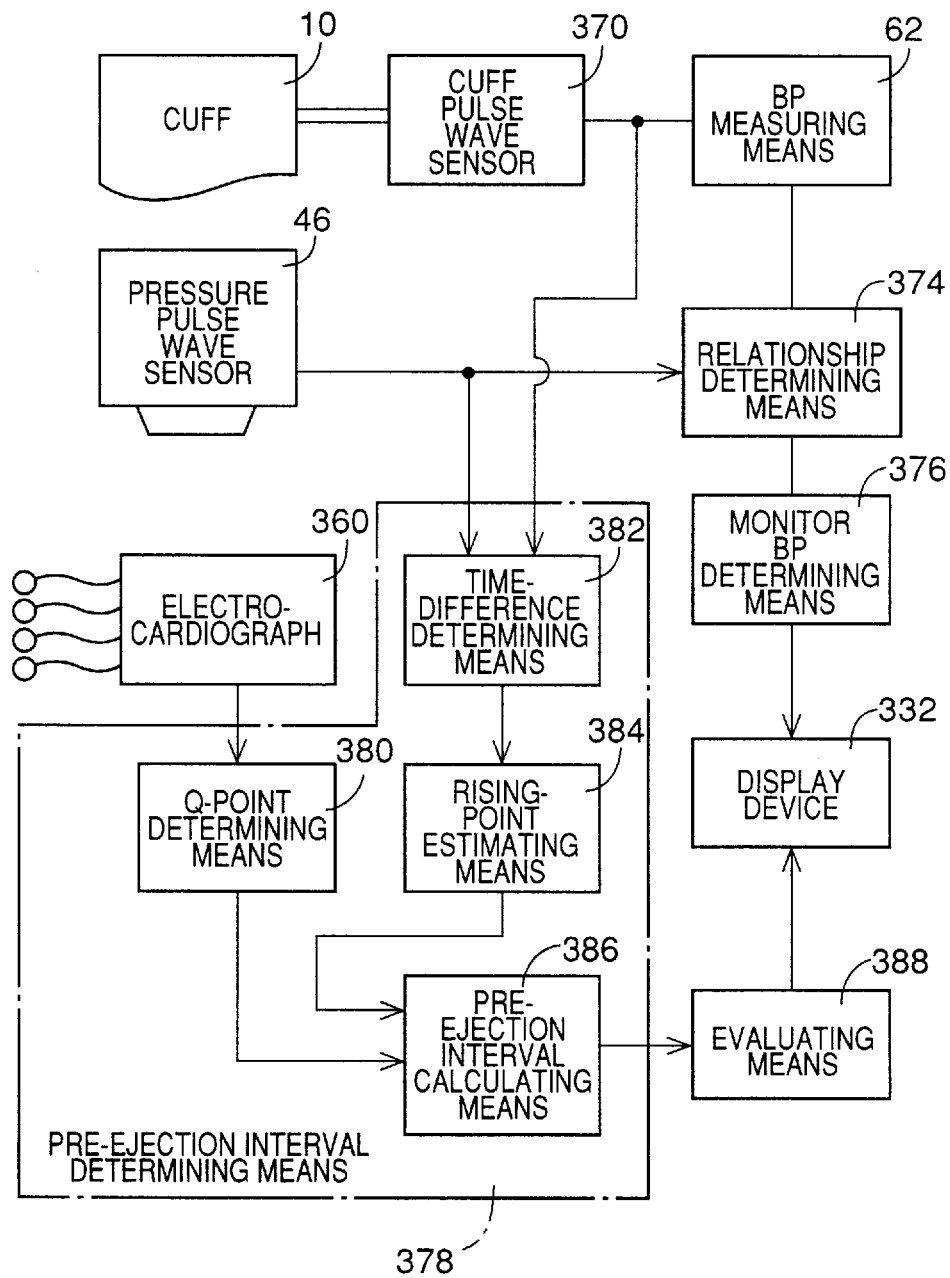
FIG. 25 is a diagrammatic view for explaining various functions of a control device of the evaluating apparatus of FIG. 24.

A cuff pulse wave ("CPW") sensor 370 shown in FIG. 25 is provided by a cuff 10, a pressure sensor 14, and a CPW filter circuit 24. Under control of the control device 328, the CPW sensor 370 detects a pressure oscillation produced in the cuff 10 in synchronism with the heartbeat of the patient, i.e., cuff pulse wave ("CPW"), with the cuff 10 being held at a predetermined pressure value lower than a diastolic BP value of the patient.

FIG. 25 illustrates various functions of the control device 328 of the present apparatus 308, i.e., BP monitor apparatus and cardiac-function evaluating apparatus. The control device 328 functions as a part of the BP measuring means 62 that is the same as the BP measuring means 62 of the first embodiment shown in FIG. 1. The control device 328 also functions as relationship determining means 374 which determines, for an individual patient, a $P_{BP}$-$P_M$ relationship between BP values $P_{BP}$ and PPW magnitudes $P_M$ that is expressed by a mathematical linear function and is shown in FIG. 3, based on at least two of a first combination of an upper-peak magnitude $P_{Hpk}$ of a heartbeat-synchronous pulse of PPW detected by a PPW sensor 46 and a systolic BP value $P_{BPSYS}$ measured by the BP measuring means 62, a second combination of a mean magnitude of the same pulse and a measured mean BP value $P_{BPMEAN}$, and a third combination of a lower-peak magnitude $P_{Lpk}$ of the same pulse and a measured diastolic BP value $P_{BPDIA}$. Monitor BP determining means 376 continuously determines a systolic and a diastolic BP value (i.e., monitor BP values, $MBP_{SYS}$, $MBP_{DIA}$) of the patient based on an upper-peak and a lower-peak magnitude $P_{Hpk}$, $P_{Lpk}$ of each of heartbeat-synchronous pulses of the PPW detected by the PPW sensor 46, according to the $P_{BP}$-$P_M$ relationship determined by the relationship determining means 376. The display device 332 continuously displays the monitor BP values MBP determined by the monitor BP determining means 376.

Pre-ejection period determining means 378 includes Q-point determining means 380, time-difference determining means 382, rising-point estimating means 384, and pre-ejection period calculating means 386, and determines a pre-ejection period, PEP, between a Q point of a heartbeat-synchronous pulse of the ECG provided by the electrocardiograph 360, and a rising point (i.e., minimum point) of a corresponding heartbeat-synchronous pulse of an intra-aortic pulse wave of the patient, based on a waveform of the ECG and respective waveforms of the CPW and PPW detected by the CPW and PPW sensors 370, 46. The rising point is a lower-peak point of each pulse of the intra-aortic pulse wave. Evaluating means 388 evaluates the blood-ejecting function of the heart of the subject based on the pre-ejection period PEP determined by the pre-ejection period determining means 378.

Figure 26:
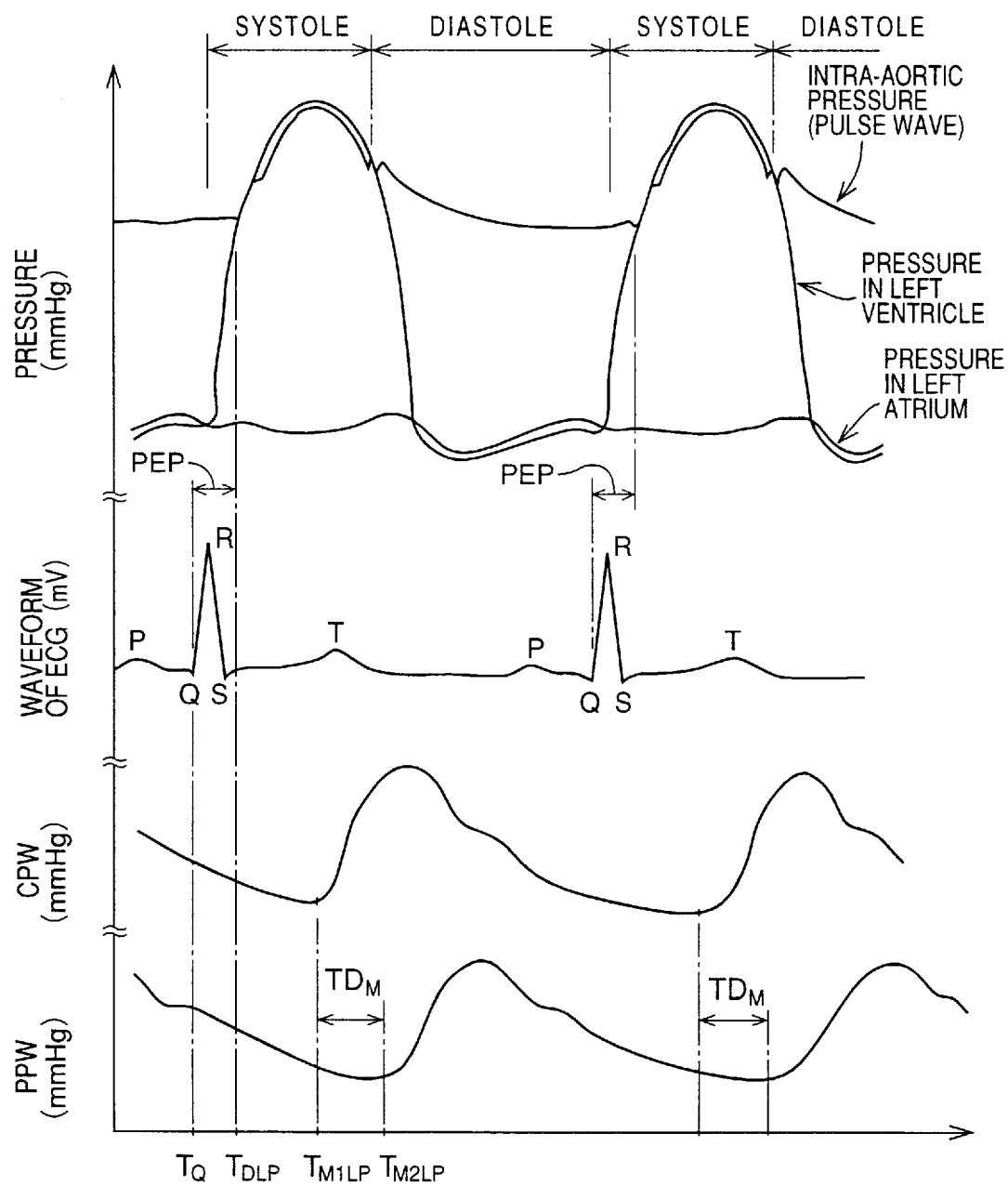
FIG. 26 is a time chart representing the waveform of electrocardiogram (ECG) provided by an electrocadiograph of the apparatus of FIG. 24, the waveform of cuff pulse wave (CPW) detected by a CPW sensor of the apparatus, and the waveform of pressure pulse wave (PPW) detected by a PPW sensor of the apparatus.

The Q-point determining means 380 determines a time, TQ, of production or detection of the Q point of each heartbeat-synchronous pulse of the ECG provided by the electrocardiograph 360. The Q point is a minimum point of a Q wave of each pulse of the ECG. On the waveform of ECG, Q point is very near to R point, i.e., maximum point of R wave, and to S point, i.e., minimum point of S wave, as shown in FIG. 26, and the time difference between Q point and each of R point and S point can be compensated, as needed. Therefore, the Q-point determining means 380 may determine R point or S point in place of Q point. Since, however, R wave most clearly shows in ECG, the Q-point determining means 380 can determine the time of occurrence of R point and estimate the time of occurrence of Q point based on the determined time of occurrence of R point with high accuracy.

The time-difference determining means 382 determines a time difference, $TD_M$, between a time of detection of a heartbeat-synchronous pulse of the CPW detected by the CPW sensor 370 and a time of detection of a corresponding heartbeat-synchronous pulse of the PPW detected by the PPW sensor 46. More specifically described, the time-difference determining means 382 specifies the respective times of detection of respective rising points (i.e., lower-peak points) or respective upper-peak points the CPW and the PPW, and determines, as the time difference $TD_M$, the difference between the determined detection times of rising points or upper-peak points of the CPW and the PPW. FIG. 26 shows the time difference $TD_M$ (=$T_{M2LP}$-$T_{M1LP}$) as the difference between a time, $T_{M1LP}$, of rising point (lower-peak point) of one pulse of the CPW and a time, $T_{M2LP}$, of rising point of a corresponding pulse of the PPW.

Figure 27:
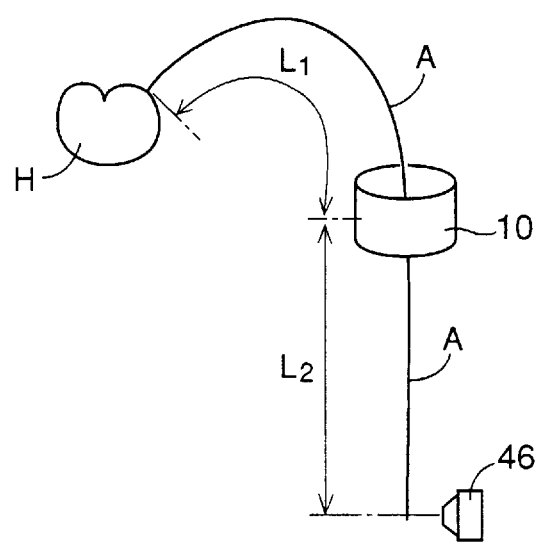
FIG. 27 is a view for explaining a mathematical expression employed by the apparatus of FIG. 24, for calculating a pre-ejection period, PEP.

The rising-point estimating means 384 estimates a time, $T_{DLP}$, of production or occurrence of rising point of each pulse of the intra-aortic pulse wave, based on the time difference $TD_M$ determined by the time-difference determining means 382. More specifically, the rising-point estimating means 384 estimates the time $T_{DLP}$ based on the actual time difference $TD_M$ according to a predetermined relationship which is pre-stored in the ROM 331 and which may be expressed by the following function (2):

$$T_{DLP}=T_{M1LP}-TD_M \cdot (k_1L_1/k_2L_2) \qquad (2)$$

where $L_1$ is the length of an artery, A, from the left ventricle of the heart, H, of the patient to the position where the cuff 10 is worn on a body portion of the patient, as shown in FIG. 27;

$L_2$ is the length of artery A from the position of the cuff 10 to the position where the PPW sensor 46 is worn on a different body portion of the same patient;

$k_1$ is a correction coefficient; and $k_2$ is a correction coefficient.

The lengths $L_1$, $L_2$ and the coefficients $k_1$, $k_2$ are predetermined based on experimental data. The coefficients $k_1$, $k_2$ compensate for the difference of respective speeds of propagation of the pulse wave through the length $L_1$ and the length $L_2$.

The pre-ejection period calculating means 386 calculates the pre-ejection period PEP (=$T_{DLP}$-$T_Q$ (msec)) by extracting the time $T_Q$ determined by the Q-point determining means 380 from the time $T_{DLP}$ estimated by the rising-point estimating means 384. The evaluating means 388 evaluates the blood-ejecting function ("BEF") of the heart H of the patient based on the thus calculated pre-ejection period PEP, and the display device 332 displays the evaluation result provided by the evaluating means 388. For example, the pre-ejection period calculating means 386 calculates a first value, $PEP_1$, of the pre-ejection period PEP when the patient is at rest, i.e., before the patient undergoes a physical exercise on an exercise device (not shown in FIG. 24; for example, the same device as the exercise device 68 shown in FIG. 1), and determines a second value, $PEP_2$, of the pre-ejection period PEP after the physical exercise. The RAM 333 includes a first memory area for storing the first value $PEP_1$, and a second memory area for storing the second value $PEP_2$. The evaluating means 388 evaluates the blood-ejecting function by comparing an amount of change, $\Delta$ PEP (=$PEP_2$-$PEP_1$), of the second value $PEP_2$ from the first value $PEP_1$, or a rate of change, $R_{PEP}$ (=$PEP_2/PEP_1$), of the second value $PEP_2$ from the first value $PEP_1$, with each of a plurality of predetermined reference values which are step-wise different from one another.

In the case where patient's heart H suffers from myocardial ischemia, the blood-ejecting function of the heart muscle is low and the pre-ejection period PEP is long. Thus, the cardiac function can be evaluated such that the greater the amount of change Δ PEP or the rate of change $R_{PEP}$ is, the lower the function is. Otherwise, the evaluating means 388 may be adapted to evaluate the cardiac function based on the time, or rate, of recovering of the second values $PEP_2$ determined after patient's exercise, back to a value substantially equal to the first value $PEP_1$ determined when the patient is at rest. The longer the recovering time is, or the lower the recovering rate is, the lower the cardiac function is.

Hereinafter, there will be described the operation of the BP monitor apparatus 308 as the cardiac-function evaluating apparatus, by reference to the flow charts of FIGS. 28 and 29. Steps SA1, SA7, and SA8 are the same as those of FIG. 8 and the description thereof is omitted.

Figure 28:
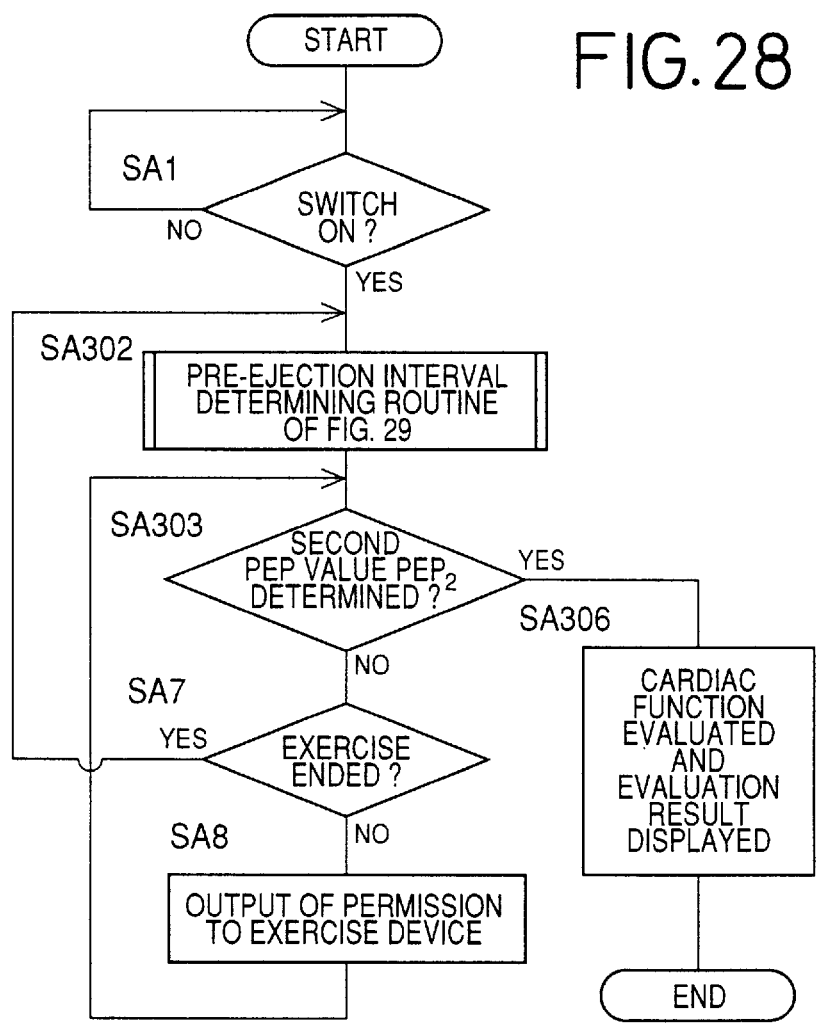
FIG. 28 is a flow chart representing a control program according to which the apparatus of FIG. 24 operates.
Figure 29:
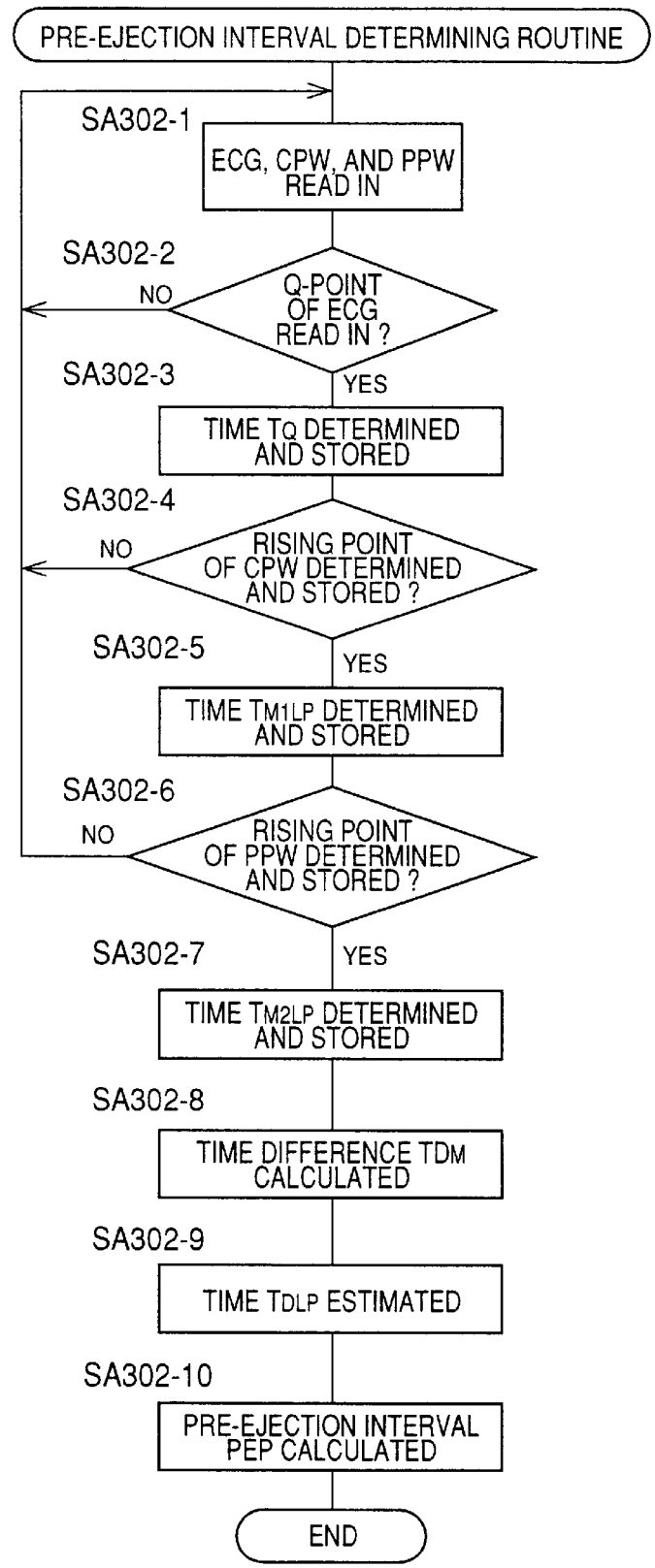
FIG. 29 is a flow chart representing a pre-ejection period determining routine of the control program of FIG. 28.

At Step SA302 of FIG. 28, the CPU 329 of the control device 328 carries out the pre-ejection period determining routine of FIG. 29. Step SA302 corresponds to the pre-ejection period determining means 378.

At Step SA302-1 of FIG. 29, the CPU 329 reads in, at predetermined sampling intervals, the ECG provided by the electrocardiograph 360, the CPW detected by the CPW sensor 370 including the cuff 10 being held at a predetermined low pressure value, and the PPW detected by the PPW sensor 46. Subsequently, at Step SA302-2, the CPU 329 judges whether the CPU 329 has read in a Q point of one heartbeat-synchronous pulse of the ECG. While negative judgments are made at Step SA302-2, Steps SA302-1 and SA302-2 are repeated. Meanwhile, if a positive judgment is made at Step SA302-2, the control of the CPU 329 goes to Step SA302-3 to determine the time $T_Q$ of occurrence or detection of the Q point and store data indicative of the determined time $T_Q$ in an appropriate area of the RAM 333. The time $T_Q$ is shown in FIG. 26. Steps SA302-2 and SA302-3 correspond to the Q-point determining means 380.

Next, at Step SA302-4, the CPU 329 judges whether the CPU 329 has read in a rising point (minimum point) of one heartbeat-synchronous pulse of the CPW detected by the CPW sensor 370. If a negative judgment is made at Step SA302-4, the control of the CPU 329 goes back to Step SA302-1. On the other hand, if a positive judgment is made at Step SA302-4, the control goes to Step SA302-5 to determine the time $T_{M1LP}$ of occurrence or detection of the rising point of the CPW and store data indicative of the determined time $T_{M1LP}$ in an area of the RAM 333. The time $T_{M1LP}$ is shown in FIG. 26.

Subsequently, at Step SA302-6, the CPU 329 judges whether the CPU 329 has read in a rising point of one heartbeat-synchronous pulse of the PPW detected by the PPW sensor 46. If a negative judgment is made at Step SA302-6, the control of the CPU 329 goes back to Step SA302-1. On the other hand, if a positive judgment is made at Step SA302-6, the control goes to Step SA302-7 to determine the time $T_{M2LP}$ of occurrence or detection of the rising point of the PPW and store data indicative of the determined time $T_{M2LP}$ in an area of the RAM 333. The time $T_{M2LP}$ is shown in FIG. 26.

At Step SA302-8, the CPU 329 calculates the time difference $TD_M$ (=$T_{M2LP}$-$T_{M1LP}$) by subtracting the time TMLLP from the time $T_{M2LP}$. Steps SA302-4 to SA302-8 correspond to the time-difference determining means 382.

At Step SA302-9, the CPU 329 estimates or calculates the time $T_{DLP}$ of occurrence of the rising point of one heartbeat-synchronous pulse of an intra-aortic pulse wave of the patient, based on the actual time difference $TD_M$ and the actual time $T_{M1LP}$ of the CPW, according to the predetermined expression (2). Step SA302-9 corresponds to the rising-point estimating means 384.

Subsequently, at Step SA302-10, the CPU 329 determines or calculates the pre-ejection period PEP (=$T_{DLP}$-$T_Q$) by subtracting the time $T_Q$ from the time $T_{DLP}$. At an early stage of operation, this PEP value is a first value $PEP_1$ determined before the patient undergoes a physical exercise, and is stored in the RAM 333.

Then, back to Step SA303 of FIG. 28, the CPU 329 judges whether a second value $PEP_2$ of the pre-ejection period PEP has been determined after the exercise. At an early stage, a negative judgment is made at Step SA303, and the control of the CPU 329 goes to Step SA7 that is the same as that of FIG. 8. At an early stage, a negative judgment is made at Step SA7, and the control of the CPU 329 goes to Step SA8 that is the same as that of FIG. 8. Step SA8 is followed by Step SA303.

While Steps SA303, SA7 and SA8 are repeated, a positive judgment is made at Step SA7, if a predetermined physical exercise ended on the exercise device. In this case, Step SA7 is followed by Step SA302 to carry out the pre-ejection period determining routine of FIG. 29 and determine a second PEP value $PEP_2$ after the exercise. The determined second value $PEP_2$ is stored in the RAM 333. Since at Step SA303 a positive judgment is made, the control of the CPU 329 goes to Step SA306 to evaluate the cardiac function of the patient based on the first and second values $PEP_1$, $PEP_2$ each determined at Step SA302. For example, the CPU 329 compares the rate of change $R_{PEP}$ with each of four reference values and selects one of five PEP ranges defined by the four reference values within which the value $R_{PEP}$ falls. The CPU 329 controls the display device 332 to display the selected PEP range within which the value $R_{PEP}$ falls. Step SA306 corresponds to the evaluating means 388.

As is apparent from the foregoing description, in the fourth embodiment, the pre-ejection period determining means 378 determines, before and after patient's exercise, the first and second pre-ejection periods $PEP_1$, $PEP_2$, respectively, based on the time $T_Q$ of the Q point of the ECG provided by the electrocardiograph 360 and the respective times $T_{M1LP}$, $T_{M2LP}$ of the CPW and the PPW provided by the CPW sensor 370 and the PPW sensor 46, and the evaluating means 388 evaluates the cardiac function of the patient based on the first and second pre-ejection periods $PEP_1$, $PEP_2$. Since the pre-ejection period PEP (PEP1, PEP2) reflects the degree of ischemia of the heart muscle of the patient, the present apparatus 308 evaluates the cardiac function of the patient with high reliability.

In the evaluating apparatus 308, the pre-ejection period determining means 378 determines the first and second values $PEP_1$, $PEP_2$ of the pre-ejection period PEP before and after patient's exercise, respectively, and the evaluating means 378 evaluates the cardiac function of the patient based on the change of the second value $PEP_2$ relative to the first value $PEP_1$. When the cardiac function of the patient is low due to myocardial ischemia, the pre-ejection period PEP does not change so much before and after patient's exercise. Thus, the present apparatus 308 can evaluate the cardiac function of the patient with high reliability.

The evaluating apparatus 308 includes the CPW and PPW sensors 370, 46 which are adapted to be worn on two predetermined positions of a patient, respectively, to detect the CPW and PPW from the patient. The pre-ejection period determining means 378 includes the time-difference determining means 382 which determines the time difference $TD_M$ (=$T_{M2LP}$-$T_{M1LP}$) of the CPW and PPW detected by the two sensors 370, 46, the Q-point determining means 380 which determines the actual Q point of the waveform of ECG, and the pre-ejection period calculating means 386 which calculates, according to the predetermined relationship, the pre-ejection period PEP based on the time $T_Q$ of the Q point and the time difference $TD_M$. Since the pre-ejection period PEP is determined based on the time $T_Q$ and the time difference $TD_M$, the period PEP is determined with high accuracy.

In the evaluating apparatus 308, the pre-ejection period determining means 378 includes the rising-point estimating means 384 which estimates the time $T_{DLP}$ of the rising point of each pulse of the intra-aortic pulse wave of the patient based on the time difference $TD_M$ calculated by the time-difference determining means 382, and the pre-ejection period calculating means 386 calculates the pre-ejection period PEP based on the time $T_Q$ of the Q point and the time $T_{DLP}$ of the rising point estimated by the rising-point estimating means 384. Thus, the period PEP can be determined with ease and accuracy.

Since the CPW sensor 370 including the cuff 10, and the PPW sensor 46, of the BP monitor apparatus 308 are also used for evaluating the cardiac function of the patient, the number of parts needed to produce the present apparatus 308 is reduced.

Although in the fourth embodiment the pre-ejection period PEP is calculated according to the expression (2), based on the time difference $TD_M$, it is possible to calculate the period PEP based on respective speeds of propagation of the CPW and PPW detected by the CPW and PPW sensors 370, 46 and the distance between two positions where the two sensors 370, 46 are worn on the patient.

In the case where a time difference, $TD_A$, between the time of occurrence of pulse wave at the left ventricle of the heart and the time of occurrence of pulse wave at the upper arm can be regarded as being substantially constant, it is possible to calculate the time $T_{DLP}$ by subtracting a predetermined constant value $TD_A$ from the actual time $T_{M1LP}$ of rising point of the CPW. In the latter case, the PPW sensor 46 may be omitted.

Since the speed of propagation of pulse wave is variable depending upon the blood pressure of the patient, it is possible to determine each of the correction coefficients $k_1$, $k_2$ as a function of actual blood pressure of the patient. In the latter case, the pre-ejection period PEP can be determined with higher accuracy.

Although in the fourth embodiment the CPW sensor 370 including the cuff 10 detects the CPW produced from the upper arm of a patient and the PPW sensor 46 detects the PPW produced from the wrist of the same arm as that on which the cuff 10 is worn, it is possible to wear the cuff 10 and the PPW sensor 46 on different arms of the patient, respectively.

While in the fourth embodiment the CPW sensor 370 including the cuff 10, and the PPW sensor 46, are used as the pulse wave sensors of the cardiac-function evaluating apparatus, it is possible to use other sorts of pulse wave sensors, for example, a photoelectric pulse wave sensor which includes a light source for irradiating the skin of a living subject and one or more light detecting elements for detecting the light reflected from, or transmitted through, the skin of the subject; or a supersonic pulse wave sensor which emits a supersonic wave toward the wall of an artery of a living subject and detects the oscillation of the arterial wall. The pulse wave sensors may be worn on any positions on the subject, so long as the two sensors detect the same pulse at different timings. In the case where the present invention is applied to a pulse oximeter including a photoelectric pulse wave sensor which detects pulse wave by emitting two sorts of lights having different wavelengths toward the skin of a subject, the photoelectric pulse wave sensor is also used for evaluating the cardiac function of the subject.

It is to be understood that the present invention may be embodied with other changes, improvements, and modifications that may occur to those skilled in the art without departing from the spirit and scope of the invention defined in the appended claims.

What is claimed is:

1. An apparatus for providing physical information relating to a blood-ejecting function of a heart of a living subject, comprising:

a pressure pulse wave sensor which is adapted to be worn on a body portion of the subject to detect a pressure pulse wave produced from an artery of the subject in synchronism with a heartbeat of the subject;

first determining means for determining a first value of an index corresponding to a systolic area which is defined by a waveform of a first heartbeat-synchronous pulse of the pressure pulse wave detected by said pressure pulse wave sensor before the subject undergoes a physical exercise;

second determining means for determining a second value of said index corresponding to a systolic area which is defined by a waveform of a second heartbeat-synchronous pulse of the pressure pulse wave detected by said pressure pulse wave sensor after the subject undergoes said physical exercise; and a display device which displays, as said physical information, the determined first and second values of said index in comparison with each other, so that an observer evaluates the blood-ejecting function of the heart of the subject based on said determined first and second values of the index displayed by said display device.

2. An apparatus according to claim 1, further comprising evaluating means for evaluating said blood-ejecting function of the heart of the subject, based on said determined first and second values of the index, and wherein said display device displays information indicative of a result of evaluation of the blood-ejecting function by said evaluating means.

3. An apparatus according to claim 1, further comprising:

a blood pressure measuring device which measures a blood pressure of the subject, said blood pressure measuring device including an inflatable cuff which is adapted to be worn on the subject; and calibrating means for determining a first relationship between blood pressure and magnitude of said pressure pulse wave, based on at least one magnitude of at least one heartbeat-synchronous pulse of the pressure pulse wave detected by said pressure pulse wave sensor before the subject undergoes said physical exercise, and at least one blood pressure value of the subject measured by said blood pressure measuring device before the subject undergoes said physical exercise, and determining a second relationship between blood pressure and magnitude of said pressure pulse wave, based on at least one magnitude of at least one heartbeat-synchronous pulse of the pressure pulse wave detected by said pressure pulse wave sensor after the subject undergoes said physical exercise, and at least one blood pressure value of the subject measured by said blood pressure measuring device after the subject undergoes said physical exercise, said calibrating means calibrating, according to said first relationship, said waveform of said first heartbeat-synchronous pulse and calibrating, according to said second relationship, said waveform of said second heartbeat-synchronous pulse, wherein said first determining means determines said first value of the index corresponding to said systolic area defined by the calibrated waveform of said first heartbeat-synchronous pulse, and said second determining means determines said second value of the index corresponding to said systolic area defined by the calibrated waveform of said second heartbeat-synchronous pulse.

4. An apparatus according to claim 1, further comprising a blood-pressure measuring device comprising:

an inflatable cuff which is adapted to be worn on the subject;

a distal and a proximal microphone which are provided at a distal and a proximal position on said cuff worn on the subject, respectively, and which detect a plurality of distal arterial sounds at said distal position and a plurality of proximal arterial sounds at said proximal position, respectively, while a pressure in said cuff is changed;

delay-time determining means for determining a delay time of a time of detection of each of said distal arterial sounds detected by said distal microphone, from a time of detection of a corresponding one of said proximal arterial sounds detected by said proximal microphone;

curve providing means for determining a product of each of respective magnitudes of said distal arterial sounds and a corresponding one of the respective delay times of the distal arterial sounds, and providing a curve by connecting the respective determined products with one another along an axis indicative of said pressure of said cuff; and blood-pressure determining means for determining a blood pressure of the subject based on the curve provided by said curve providing means.

5. An apparatus for evaluating a blood-ejecting function of a heart of a living subject, comprising:

a pressure pulse wave sensor which is adapted to be worn on a body portion of the subject to detect a pressure pulse wave which is produced from an artery of the subject in synchronism with a heartbeat of the subject;

first determining means for determining a first value of an index corresponding to a systolic area which is defined by a waveform of a first heartbeat-synchronous pulse of the pressure pulse wave detected by said pressure pulse wave sensor before the subject undergoes a physical exercise;

second determining means for determining a second value of said index corresponding to a systolic area which is defined by a waveform of a second heartbeat-synchronous pulse of the pressure pulse wave detected by said pressure pulse wave sensor after the subject undergoes said physical exercise; and evaluating means for evaluating said blood-ejecting function of the heart of the subject, based on the determined first and second values of said index.

6. An apparatus according to claim 5, wherein said evaluating means comprises first means for evaluating said blood-ejecting function of the heart of the subject, based on at least one of an amount of change of said determined second value from said determined first value and a rate of change of the determined second value from the determined first value.

7. An apparatus according to claim 6, wherein said first means of said evaluating means comprises judging means for judging whether said blood-ejecting function of the heart of the subject is normal, by comparing said one of said amount of change and said rate of change with a corresponding one of a first reference value and a second reference value.

8. An apparatus according to claim 5, wherein said second determining means comprises means for determining a plurality of said second values of the index each of which corresponds to a systolic area defined by a waveform of a corresponding one of a plurality of said second heartbeat-synchronous pulses of the pressure pulse wave detected by said pressure pulse wave sensor after the subject undergoes said physical exercise, and wherein said evaluating means comprises second means for evaluating said blood-ejecting function of the heart of the subject, based on at least one of a time of recovering of the determined second values back to a value substantially equal to said determined first value and a rate of recovering of said determined second values back to a value substantially equal to the determined first value.

9. An apparatus according to claim 8, wherein said second means of said evaluating means comprises judging means for judging whether said blood-ejecting function of the heart of the subject is normal, by comparing said one of said time of recovering and said rate of recovering with a corresponding one of a third reference value and a fourth reference value.

10. An apparatus according to claim 5, further comprising converting means for converting said waveform of each of said first and second heartbeat-synchronous pulses, to a converted waveform, according to a predetermined mathematical transfer function defining a relationship between a waveform of a heartbeat-synchronous pulse of a pulse wave detected in an aorta of the subject and a waveform of a corresponding heartbeat-synchronous pulse of a pulse wave detected from said artery of said body portion of the subject, wherein said first determining means determines said first value of the index corresponding to said systolic area defined by said converted waveform of said first heartbeat-synchronous pulse, and said second determining means determines said second value of the index corresponding to said systolic area defined by said converted waveform of said second heartbeat-synchronous pulse.

11. An apparatus according to claim 5, further comprising:

a blood pressure measuring device which measures a blood pressure of the subject, said blood pressure measuring device including an inflatable cuff which is adapted to be worn on the subject; and calibrating means for determining a first relationship between blood pressure and magnitude of said pressure pulse wave, based on at least one magnitude of at least one heartbeat-synchronous pulse of the pressure pulse wave detected by said pressure pulse wave sensor before the subject undergoes said physical exercise, and at least one blood pressure value of the subject measured by said blood pressure measuring device before the subject undergoes said physical exercise, and determining a second relationship between blood pressure and magnitude of said pressure pulse wave, based on at least one magnitude of at least one heartbeat-synchronous pulse of the pressure pulse wave detected by said pressure pulse wave sensor after the subject undergoes said physical exercise, and at least one blood pressure value of the subject measured by said blood pressure measuring device after the subject undergoes said physical exercise, said calibrating means calibrating, according to said first relationship, said waveform of said first heartbeat-synchronous pulse and calibrating, according to said second relationship, said waveform of said second heartbeat-synchronous pulse, wherein said first determining means determines said first value of the index corresponding to said systolic area defined by the calibrated waveform of said first heartbeat-synchronous pulse, and said second determining means determines said second value of the index corresponding to said systolic area defined by the calibrated waveform of said second heartbeat-synchronous pulse.

12. An apparatus according to claim 5, further comprising a blood-pressure measuring device comprising:

an inflatable cuff which is adapted to be worn on the subject;

a distal and a proximal microphone which are provided at a distal and a proximal position on said cuff worn on the subject, respectively, and which detect a plurality of distal arterial sounds at said distal position and a plurality of proximal arterial sounds at said proximal position, respectively, while a pressure in said cuff is changed;

delay-time determining means for determining a delay time of a time of detection of each of said distal arterial sounds detected by said distal microphone, from a time of detection of a corresponding one of said proximal arterial sounds detected by said proximal microphone;

curve providing means for determining a product of each of respective magnitudes of said distal arterial sounds and a corresponding one of the respective delay times of the distal arterial sounds, and providing a curve by connecting the respective determined products with one another along an axis indicative of said pressure of said cuff; and blood-pressure determining means for determining a blood pressure of the subject based on the curve provided by said curve providing means.

13. An apparatus for providing physical information relating to a myocardial ischemia of a heart of a living subject, comprising:

a continuous blood-pressure measuring device which continuously measures a blood pressure of the subject, thereby providing continuously measured blood-pressure values of the subject;

first frequency-analysis means for analyzing respective frequencies of a plurality of blood-pressure fluctuating components occurring in said continuously measured blood-pressure values, thereby providing a frequency spectrum of said blood-pressure fluctuating components, said first frequency-analysis means extracting, from said continuously measured blood-pressure values, a first one of said blood-pressure fluctuating components which has a frequency lower than a frequency of a second one of said blood-pressure fluctuating components which corresponds to a respiration of the subject; and a display device which displays, as said physical information, at least one of (a1) the first blood-pressure fluctuating component extracted from the continuously measured blood pressure values provided by said blood-pressure measuring device before the subject undergoes a physical exercise and (a2) a first value of an index derived from the first blood-pressure fluctuating component obtained before the exercise, and at least one of (b1) the first blood-pressure fluctuating component extracted from the continuously measured blood pressure values provided by said blood-pressure measuring device after the subject undergoes said physical exercise and (b2) a second value of said index derived from the first blood-pressure fluctuating component obtained after the exercise, in comparison with each other, so that an observer evaluates the myocardial ischemia of the heart of the subject based on said one of said first blood-pressure fluctuating component obtained before said exercise and said first value of the index and said one of said first blood-pressure fluctuating component obtained after said exercise and said second value of the index displayed by said display device.

14. An apparatus according to claim 13, further comprising:

a continuous pulse-interval measuring device which continuously measures a time interval between successive two heartbeat-synchronous pulses of a pulse wave of the subject, thereby providing continuously measured pulse-interval values of the subject;

second frequency-analysis means for analyzing respective frequencies of a plurality of pulse-interval fluctuating components occurring in said continuously measured pulse-interval values, thereby providing a frequency spectrum of said pulse-interval fluctuating components, said second frequency-analysis means extracting, from said continuously measured pulse-interval values, one of said pulse-interval fluctuating components which has a frequency substantially equal to the frequency of said second blood-pressure fluctuating component which corresponds to the respiration of the subject; and means for determining, as said first value of the index, a ratio of a magnitude of the first blood-pressure fluctuating component to a magnitude of the one pulse-interval fluctuating component both of which are obtained before said exercise, and determining, as said second value of the index, a ratio of a magnitude of the first blood-pressure fluctuating component to a magnitude of the one pulse-interval fluctuating component both of which are obtained after said exercise.

15. An apparatus according to claim 14, wherein said first frequency-analysis means comprises means for producing a signal representing said first blood-pressure fluctuating component, and said second frequency-analysis means comprises means for producing a signal representing said one pulse-interval fluctuating component.

16. An apparatus for evaluating a myocardial ischemia of a heart of a living subject, comprising:

a continuous blood-pressure measuring device which continuously measures a blood pressure of the subject, thereby providing continuously measured blood pressure values of the subject;

first frequency-analysis means for analyzing respective frequencies of a plurality of blood-pressure fluctuating components occurring in said continuously measured blood pressure values, thereby providing a frequency spectrum of said blood-pressure fluctuating components, said first frequency-analysis means extracting, from said continuously measured blood pressure values, a first one of said blood-pressure fluctuating components which has a frequency lower than a frequency of a second one of said blood-pressure fluctuating components which corresponds to a respiration of the subject; and evaluating means for evaluating the myocardial ischemia of the subject based on at least one of (a1) the first blood-pressure fluctuating component extracted from the continuously measured blood pressure values provided by said blood-pressure measuring device before the subject undergoes a physical exercise and (a2) a first value of an index derived from the first blood-pressure fluctuating component obtained before the exercise, and at least one of (b1) the first blood-pressure fluctuating component extracted from the continuously measured blood pressure values provided by said blood-pressure measuring device after the subject undergoes said physical exercise and (b2) a second value of said index derived from the first blood-pressure fluctuating component obtained after the exercise.

17. An apparatus according to claim 16, wherein said continuous blood-pressure measuring device comprises a pressure pulse wave sensor which is adapted to be worn on a body portion of the subject to detect a pressure pulse wave which is produced from an artery of the subject in synchronism with a heartbeat of the subject, and means for continuously determining, as said continuously measured blood-pressure values, a systolic blood-pressure value of the subject based on an upper-peak magnitude of each of a plurality of heartbeat-synchronous pulses of the pressure pulse wave detected by said pressure pulse wave sensor.

18. An apparatus according to claim 16, further comprising:
  a continuous pulse-interval measuring device which continuously measures a time interval between successive two heartbeat-synchronous pulses of a pulse wave of the subject, thereby providing continuously measured pulse-interval values of the subject; and
  second frequency-analysis means for analyzing respective frequencies of a plurality of pulse-interval fluctuating components occurring in said continuously measured pulse-interval values, thereby providing a frequency spectrum of said pulse-interval fluctuating components, said second frequency-analysis means extracting, from said continuously measured pulse-interval values, one of said pulse-interval fluctuating components which has a frequency substantially equal to the frequency of said second blood-pressure fluctuating component which corresponds to the respiration of the subject,
  wherein said evaluating means comprises means for determining, as said first value of the index, a first ratio of a magnitude of the first blood-pressure fluctuating component to a magnitude of the one pulse-interval fluctuating component both of which are obtained before the exercise, and determining, as said second value of the index, a second ratio of a magnitude of the first blood-pressure fluctuating component to a magnitude of the one pulse-interval fluctuating component both of which are obtained after the exercise.

19. An apparatus according to claim 18, wherein said first frequency-analysis means comprises means for producing a signal representing said first blood-pressure fluctuating component, and said second frequency-analysis means comprises means for producing a signal representing said one pulse-interval fluctuating component.

20. An apparatus according to claim 18, wherein said evaluating means comprises means for evaluating the myocardial ischemia by judging whether at least one of an amount of change of said second ratio from said first ratio and a rate of change of said second ratio from said first ratio is greater than a corresponding one of a first reference value and a second reference value.

21. An apparatus according to claim 18, wherein said evaluating means comprises means for determining a plurality of said second ratios after the subject undergoes said physical exercise, and evaluating the myocardial ischemia of the subject, based on at least one of a time of recovering of the determined second ratios back to a value substantially equal to said first ratio and a rate of recovering of said determined second ratios back to a value substantially equal to said determined first ratio.

22. An apparatus according to claim 18, wherein said continuous pulse-interval measuring device comprises a pressure pulse wave sensor which is adapted to be worn on a body portion of the subject to detect a pressure pulse wave which is produced from an artery of the subject in synchronism with a heartbeat of the subject, and means for continuously determining, as said continuously measured pulse-interval values, a time interval between respective upper peaks of each pair of successive two pulses of a plurality of heartbeat-synchronous pulses of the pressure pulse wave detected by said pressure pulse wave sensor.

23. An apparatus for evaluating a blood-ejecting function of a heart of a living subject, comprising:
  an electrocardiograph which provides an electrocardiogram of the subject;
  at least one pulse-wave sensor which is adapted to be worn on the subject to detect at least one pulse wave from the subject;
  pre-ejection period determining means for determining a pre-ejection period between a Q point of a heartbeat-synchronous pulse of the electrocardiogram provided by said electrocardiograph, and a minimum point of a corresponding heartbeat-synchronous pulse of an intra-aortic pulse wave of the subject, based on a waveform of said electrocardiogram and a waveform of the pulse wave detected by said pulse-wave sensor; and
  evaluating means for evaluating the blood-ejecting function of the heart of the subject based on the pre-ejection period determined by said pre-ejection period determining means.

24. An apparatus according to claim 23, wherein said pre-ejection period determining means comprises means for determining a first value of said pre-ejection period before the subject undergoes a physical exercise, and determining a second value of said pre-ejection period after the subject undergoes said physical exercise, and said evaluating means comprises means for evaluating said blood-ejecting function based on a change of said second value of said pre-ejection period relative to said first value of the pre-ejection period.

25. An apparatus according to claim 23, wherein said at least one pulse-wave sensor comprises a first and a second pulse-wave sensor which are adapted to be worn on a first and a second predetermined position on the subject, respectively, to detect a first and a second pulse wave from the subject, respectively.

26. An apparatus according to claim 25, wherein said pre-ejection period determining means comprises:
  time-difference determining means for determining a time difference between a time of detection of a heartbeat-synchronous pulse of said first pulse wave detected by said first pulse wave sensor and a time of detection of a corresponding heartbeat-synchronous pulse of said second pulse wave detected by said second pulse wave sensor,
  Q-point determining means for determining a first time of production of said Q point of said heartbeat-synchronous pulse of the electrocardiogram, and
  pre-ejection period calculating means for calculating said pre-ejection period based on said first time of said Q point determined by said Q-point determining means and said time difference determined by said time-difference determining means.

27. An apparatus according to claim 26, wherein said pre-ejection period determining means further comprises minimum-point estimating means for estimating a second time of production of said minimum point of said corresponding heartbeat-synchronous pulse of said intra-aortic pulse wave, based on said time difference determined by said time-difference determining means, wherein said pre-ejection period calculating means calculates said pre-ejection period based on said first time determined by said Q-point determining means and said second time estimated by said minimum-point estimating means.

* * * * *